(12) United States Patent
Tharaux et al.

(10) Patent No.: US 8,198,266 B2
(45) Date of Patent: Jun. 12, 2012

(54) USE OF AN EGFR ANTAGONIST FOR THE TREATMENT OF GLOMEROLONEPHRITIS

(75) Inventors: Pierre Louis Tharaux, Clamart (FR); Martin Flamant, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 365 days.

(21) Appl. No.: 12/447,498

(22) PCT Filed: Oct. 31, 2006

(86) PCT No.: PCT/IB2006/003915
§ 371 (c)(1),
(2), (4) Date: Dec. 4, 2009

(87) PCT Pub. No.: WO2008/053270
PCT Pub. Date: May 8, 2008

(65) Prior Publication Data
US 2010/0104558 A1    Apr. 29, 2010

(51) Int. Cl.
*A61K 31/33*    (2006.01)
(52) U.S. Cl. .................................... 514/183
(58) Field of Classification Search .................. None
See application file for complete search history.

(56) References Cited

U.S. PATENT DOCUMENTS
7,547,781 B2 *  6/2009  Qian et al. ................. 544/293

FOREIGN PATENT DOCUMENTS
| WO | 02/16351 | 2/2002 |
| WO | 2004/056847 | 7/2004 |
| WO | 2006/002422 | 1/2006 |
| WO | 2007/011702 | 1/2007 |

OTHER PUBLICATIONS

International Search Report in PCT/IB06/03915, dated Apr. 23, 2008.
Fabian et al., Nat. Biotechnol., 23(3):329-336 (2005).
Baselga, The Oncologist, 7(Suppl 4):2-8 (2002).
Takemura et al., J. Pathol., 189(3):431-438 (1999).
Feng et al., J. Clin. Invest., 105(3):341-350 (2000).

* cited by examiner

*Primary Examiner* — Michael Pak
(74) *Attorney, Agent, or Firm* — McAndrews, Held & Malloy Ltd.

(57) ABSTRACT

The present invention relates to uses, methods and compositions for treating immune-mediated glomerulonephritis, such as crescentic glomerulonephritis. More specifically, the invention relates to the use of an EFGR antagonist or of an inhibitor of EGFR or HB-EGF expression for the treatment of said diseases.

2 Claims, 6 Drawing Sheets

USE OF AN EGFR ANTAGONIST FOR THE TREATMENT OF GLOMEROLONEPHRITIS

Figure 1:
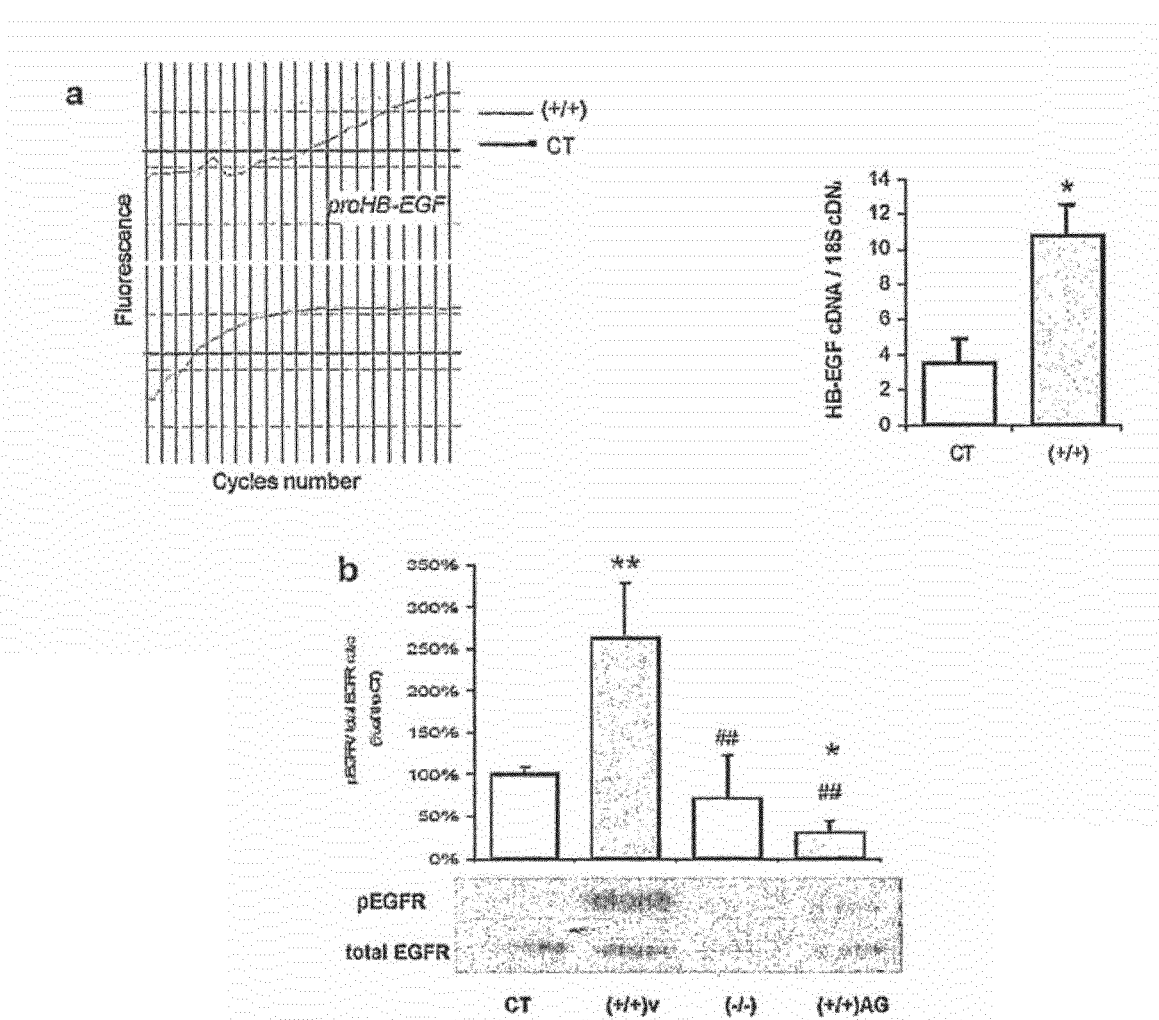

The present application is filed pursuant to 35 U.S.C. 371 as a U.S. National Phase application of International Patent Application No. PCT/IB06/03915, which was filed Oct. 31, 2006. The entire text of the aforementioned application is incorporated herein by reference in its entirety.

The present invention relates to uses, methods and compositions for treating immune-mediated glomerulonephritis, such as crescentic glomerulonephritis. More specifically, the invention relates to the use of an EFGR antagonist or of an inhibitor of EGFR or HB-EGF expression for the treatment of said diseases.

Glomerulonephritis (GN) is the term applied to a group of diseases characterised by inflammatory changes in glomerular capillaries and accompanying signs and symptoms of an acute nephritic syndrome. Glomerulonephritis may occur as a primary renal disease or as a manifestation of renal involvement in a systemic disease process, commonly vasculitis. The causative agents in most forms of human glomerulonephritis are unknown, but some evidences show that glomerulonephritis follow bacterial or viral infections. Most evidence now suggests that infectious agents, and doubtless other stimuli as well, induce glomerulonephritis by triggering an autoimmune response that results in formation of immune-complex deposits in glomeruli or elicits a cell-mediated immune response to antigens in, or of, the glomerulus (Couser W G, 1998).

The classic example of glomerulonephritis is the crescentic glomerulonephritis, also known as rapidly progressive glomerulonephritis that is induced by development of anti-glomerular basement membrane (anti-GBM) antibodies. When accompanied by pulmonary haemorrhage the condition is known as Goodpasture's syndrome.

Glomerular damage in glomerulonephritis occurs in two phases. During the acute phase, as immune reactions take place in glomeruli, a variety of mediators of tissue injury are activated. Of particular importance are complement, which generates chemotactic factors that lead to leucocyte recruitment, and C5b-9, which directly damages glomerular cells; coagulation factors that lead to fibrin deposition and crescent formation; and local and systemic release of growth factors and cytokines, which lead to activation and injury of glomerular cells. A secondary component of the acute phase of injury that leads to the chronic phase is the result of the response of glomerular cells themselves to these mediators. This involves cell proliferation with overproduction of oxidants and proteases, changes in phenotype, and overproduction of extracellular matrix, which results in sclerosis and permanently impaired renal function (Johnson R J, 1994)). Renal damage in the chronic-progressive phase of glomerulonephritis is mediated not by an acute inflammatory process but rather by non-immune mechanisms that develop as a result of loss of filtering-surface with accompanying increases in glomerular pressures in remaining nephrons. These features lead to glomerular sclerosis as well as to chronic interstitial fibrosis, which is a consequence of multiple injurious events including ischaemia, glomerular cytokine release, and toxic effects of increased protein filtration on tubules (Couser W G et al. 1994).

Symptoms of GN include: proteinuria; reduced glomerular filtration rate (GFR); serum electrolyte changes including azotemia (uremia, excessive blood urea nitrogen—BUN) and salt retention, leading to water retention resulting in hypertension and oedema; hematuria and abnormal urinary sediments including red cell casts; hypoalbuminemia; hyperlipidemia; and lipiduria.

Current treatments for glomerulonephritis include corticosteroid administration, typically as high doses of "pulse" intravenous methylprednisolone or oral prednisone therapy. This kind of treatment is currently considered the most effective pharmacologic agent available for the treatment of GN. Such steroid therapy is often administered in combination with cytotoxic general immunosuppressive agents such as azathioprine or cyclophosphamide. The overall immune suppression and resulting increased susceptibility to infection, along with other debilitating side effects associated with both steroid and cytotoxic drug administration, limit the effective use of these drugs. Aspirin-like non-steroidal anti-inflammatory drugs (NSAIDs) have also been used to reduce the glomerular inflammation and enlargement of glomerulonephritis. These drugs are not routinely used for this purpose, however, probably because of their relatively weak anti-inflammatory effects and propensity to cause gastrointestinal and other side effects in many patients. The administration of anticoagulants such as heparin or warfarin sodium, and antithrombotic agents such as cyproheptadine, dipyridamole, or sulfinpyrazone, has been used on the basis of evidence suggesting the involvement of the coagulation process in the genesis of glomerular crescents. However, objective evidence of benefit from such therapies in animals afflicted with experimentally induced crescentic glomerulonephritis has been inconsistent. Also, anticoagulants are dangerous drugs, as they can potentiate life-threatening bleeding episodes. They are especially hazardous in this regard in patients with advanced renal failure.

Therefore, there is currently no efficient treatment to stop or reverse the course of glomerulonephritis. Thus, new methods for the treatment of such a disease that are effective and convenient are really needed. An understanding of the mechanisms of glomerulonephritis would therefore help in the development of therapeutic strategies for these diseases.

A recent study provides the evidence that the Heparin-Binding Epidermal Growth Factor-like growth factor (HB-EGF) is synthesised and expressed by mesangial cells and stimulates mesangial cell proliferation during human glomerulonephritis (Takemura T et al. 1999). Furthermore, based on the experimental anti-GBM model of glomerulonephritis, Feng et al. (Feng L et al. 2000) found that HB-EGF is transcribed and expressed in high levels in glomeruli in both epithelial and mesangial cells within 30 minutes after administration of anti-GBM antibodies coincident with the onset of the glomerular hemodynamic alterations. In addition, the study shows that an antibody against HB-EGF administered just before anti-GBM antibodies blocked the fall in Single Nephron Glomerular Filtration Rate (SNGFR) and Glomerular Filtration Rate (GFR) at 90 minutes without nay change in the glomerular histologic response. However, the evoked pathophysiological roles of HB-EGF and the EGF receptor (EGFR) in the kidney have been restricted to cell proliferation and modulation of vasomotor tone with no effect on major end-points so far.

Now, the present invention provides a new method for the treatment of glomerulonephritis. The inventors have found that HB-EGF renal expression was markedly up-regulated at 3-10 days after the onset of crescentic glomerulonephritis along with sustained phosphorylation of the EGFR in glomeruli. HB-EGF deficient mice did not exhibit activation of the EGFR and presented fewer albuminuria, asciitis, renal failure and crescentic glomeruli. They have further demonstrated that survival was poorer in HB-EGF expressing mice than in HB-EGF deficient ones. Finally, the inventors have showed that administration of an EGFR tyrosine kinase inhibitor (AG1478) in wild type mice suppressed albuminuria and glomerular injury and prevented renal failure and death. These data unravel a prominent pathophysiological role for the EGFR in acute crescentic glomerulonephritis and suggest that inhibitors of the HB-EGF-EGFR cascade may be needed for preventing severe renal damage and renal failure.

Therefore an object of the invention thus relates to the use of an EGFR antagonist for the manufacture of a medicament intended for the treatment of immune-mediated glomerulonephritis A second object of the invention relates to the use of an inhibitor of EGFR, or HB-EGF expression for the manufacture of a medicament for the treatment of immune-mediated glomerulonephritis In a particular embodiment of the invention, said immune-mediated glomerulonephritis is the crescentic glomerulonephritis Definitions A "coding sequence" or a sequence "encoding" an expression product, such as an RNA, polypeptide, protein, or enzyme, is a nucleotide sequence that, when expressed, results in the production of that RNA, polypeptide, protein, or enzyme, i.e., the nucleotide sequence encode an amino acid sequence for that polypeptide, protein or enzyme. A coding sequence for a protein may include a start codon (usually ATG) and a stop codon.

As used herein, references to specific proteins (e.g., EGFR or HBEGF) can include a polypeptide having a native amino acid sequence, as well as variants and modified forms regardless of their origin or mode of preparation. A protein that has a native amino acid sequence is a protein having the same amino acid sequence as obtained from nature (e.g., EGFR or HBEGF). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including postranslational modifications. A native sequence protein includes proteins following post-translational modifications such as glycosylation, or phosphorylation, or other modifications of some amino acid residues.

Variants refer to proteins that are functional equivalents to a native sequence protein that have similar amino acid sequences and retain, to some extent, one or more activities of the native protein. Variants also include fragments that retain activity. Variants also include proteins that are substantially identical (e.g., that have 80, 85, 90, 95, 97, 98, 99%, sequence identity) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. The variations can be made using methods known in the art such as site-directed mutagenesis (Carter, et al. (1986) Nucl. Acids Res. 13:4331; Zoller et al. (1987) Nucl. Acids Res. 10:6487), cassette mutagenesis (Wells et al. (1985) Gene 34:315), restriction selection mutagenesis (Wells, et al. (1986) Philos. Trans. R. Soc. London SerA 317:415), and PCR mutagenesis (Sambrook et al., Molecular Cloning: A Laboratory Manual, 3rd edition, Cold Spring Harbor Press, N.Y., (2001)).

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., EGFR) modified by, for example, methylation, acetylation, phosphorylation, ubiquitination, SUMOylation, ADP-ribosylation, myristilation, and glycosylation.

An 'inhibitor of expression" refers to a natural or synthetic compound that has a biological effect to inhibit the expression of a gene.

A "receptor" or "receptor molecule" is a soluble or membrane bound/associated protein or glycoprotein comprising one or more domains to which a ligand binds to form a receptor-ligand complex. By binding the ligand, which may be an agonist or an antagonist the receptor is activated or inactivated and may initiate or block pathway signaling.

By "ligand" or "receptor ligand" is meant a natural or synthetic compound which binds a receptor molecule to form a receptor-ligand complex. The term ligand includes agonists, antagonists, and compounds with partial agonist/antagonist action.

An "agonist" or "receptor agonist" is a natural or synthetic compound which binds the receptor to form a receptor-agonist complex by activating said receptor and receptor-agonist complex, respectively, initiating a pathway signaling and further biological processes.

By "antagonist" or "receptor antagonist" is meant a natural or synthetic compound that has a biological effect opposite to that of an agonist. An antagonist binds the receptor and blocks the action of a receptor agonist by competing with the agonist for receptor. An antagonist is defined by its ability to block the actions of an agonist.

The term "ErbB" or "HER" refers to a receptor protein tyrosine kinase which belongs, to the ErbB receptor family and includes ErbB1 (or HER1 or EGFR), ErbB2 (or HER2), ErbB3 (or HER 3) and ErbB4 (or HER 4) receptors (Ullrich, 1984). The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a native sequence ErbB receptor or an amino acid sequence variant thereof. Preferably the ErbB receptor is native sequence human ErbB receptor. Being activated by their six structurally related agonists EGF, tumor growth factor α (TGFα), heparin-binding EGF-like growth factor (HB-EGF), amphiregulin, betacellulin and epiregulin—the receptors promote pathways entailing proliferation and transformation. Activated EGFRs homo- or heterodimerize and subsequently autophosphorylation of cytoplasmic tyrosine residues is initiated. These phosphorylated amino acids represent docking sites for a variety of different proteins (Prenzel 2001). Phosphorylated EGFR recruits adaptor proteins like Shc and Grb2 which become associated with the RasGEF Sos thus leading to GTP-loading of the small G protein Ras.

The expressions "ErbB1" and "HER1" and "EGFR" are used interchangeably herein and refer to human EGFR protein.

The term "ErbB antagonist" refers to any ErbB antagonist that is currently known in the art or that will be identified in the future, and includes any chemical entity that, upon administration to a patient, results in inhibition of a biological activity associated with activation of the ErbB in the patient, including any of the downstream biological effects otherwise resulting from the binding to ErbB of its natural ligand. Such ErbB antagonist includes any agent that can block ErbB activation or any of the downstream biological effects of ErbB activation. Such an antagonist can act by binding directly to the intracellular domain of the receptor and inhibiting its kinase activity. Alternatively, such an antagonist can act by occupying the ligand binding site or a portion thereof of the ErbB receptor, thereby making the receptor inaccessible to its natural ligand so that its normal biological activity is prevented or reduced. Alternatively, such an inhibitor can act by modulating the dimerization of ErbB polypeptides, or interaction of ErbB polypeptide with other proteins. Therefore the term "EGFR antagonist" or "Erb1 antagonist" or "HER1 antagonist" refers to an antagonist of the EGFR protein.

The term "HB-EGF" denotes the heparin-binding Epidermal Growth Factor-like growth factor. HB-EGF is a member of the Epidermal Growth Factor (EGF) family of growth factors that binds to and activates EGFR/Erb1 and ErbB4 (Higashiyama et al., 1991; Elenius et al., 1997). HB-EGF is synthesized as a type I transmembrane protein (proHB-EGF) composed of a signal peptide, propeptide, heparin-binding, EGF-like, juxtamembrane, transmembrane, and cytoplasmic domains (Higashiyama et al., 1992). Like other EGF family members (Massague and Pandiella, 1993), the membrane-anchored form of proHB-EGF is cleaved at the juxtamembrane domain, resulting in the shedding of soluble HB-EGF (sHB-EGF) (Goishi et al., 1995). ProHB-EGF is biologically active as a juxtacrine growth factor that signals to neighboring cells in a non-diffusible manner (Higashiyama et al., 1995; Iwamoto et al., 1999; Iwamoto and Mekada, 2000). It forms complexes with CD9 and integrin α3β1 on the cell membrane (Nakamura et al., 1995), and it also functions as the receptor for diphtheria toxin (DT), mediating the entry of DT into the cytoplasm (Naglich et al., 1992; Iwamoto et al., 1994). sHB-EGF is a potent mitogen and chemoattractant for a number of cell types including vascular smooth muscle cells, fibroblasts and keratinocytes (Higashiyama et al., 1993; Raab and Klagsbrun, 1997). HB-EGF has been implicated in a number of physiological and pathological processes, which include eyelid closure (Mine et al., 2005), wound healing (Shirakata et al., 2005; Marikovsky et al., 1993; Tokumaru et al., 2000), retinoid-induced skin hyperplasia (Kimura et al., 2005), cardiac hypertrophy (Asakura et al., 2002), smooth muscle cell hyperplasia (Miyagawa et al., 1995), kidney collecting duct morphogenesis (Takemura et al., 2001), blastocyst implantation (Das et al., 1994), pulmonary hypertension (Powell et al., 1993), and oncogenic transformation (Fu et al., 1999).

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

By "purified" and "isolated" it is meant, when referring to a polypeptide (i.e. interferon) or a nucleotide sequence, that the indicated molecule is present in the substantial absence of other biological macromolecules of the same type. The term "purified" as used herein preferably means at least 75% by weight, more preferably at least 85% by weight, still preferably at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, and a primate. Preferably a subject according to the invention is a human.

Therapeutic Methods and Uses

The present invention provides for methods and compositions (such as pharmaceutical compositions) for treating glomerulonephritis.

Thus an object of the invention is the use of an EGFR antagonist for the manufacture of a medicament intended for treating glomerulonephritis.

In one embodiment, the EGFR antagonist may be a low molecular weight antagonist.

Low molecular weight EGFR antagonists that may be used by the invention include, for example quinazoline EGFR antagonists, pyrido-pyrimidine EGFR antagonists, pyrimido-pyrimidine EGFR antagonists, pyrrolo-pyrimidine EGFR antagonists, pyrazolo-pyrimidine EGFR antagonists, phenylamino-pyrimidine EGFR antagonists, oxindole EGFR antagonists, indolocarbazole EGFR antagonists, phthalazine EGFR antagonists, isoflavone EGFR antagonists, quinalone EGFR antagonists, and tyrphostin EGFR antagonists, such as those described in the following patent publications, and all pharmaceutically acceptable salts and solvates of said EGFR antagonists: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652.

Additional non-limiting examples of low molecular weight EGFR antagonists include any of the EGFR antagonists described in Traxler, P (1998) and those described in Al-Obeidi F A et al. (2000).

In one embodiment, the EGFR antagonist is selected in the group consisting of erlotinib, gefitinib, canertinib, PD169540, PD-158780, AG1478, PD153035, CGP59326, PKI166; EKB569, or GW572016

A specific example of low molecular weight EGFR antagonist that can be used according to the present invention may be the [6,7-bis(2-methoxyethoxy)-4-quinazolin-4-yl]-(3-ethynylphenyl)amine (also known as OSI-774, erlotinib, or TARCEVA® (erlotinib HCl); OSI Pharmaceuticals/Genentech/Roche) (U.S. Pat. No. 5,747,498; International Patent Publication No. WO 01/34574, and Moyer J D. et al. (1997)). Tarceva has the structure of the Formula:

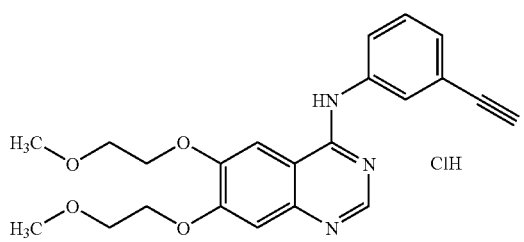

Another specific example of a low molecular weight EGFR antagonist that can be used according to the present invention may be gefitinib (also known as ZD1839 or IRESSA®; Astrazeneca) (Woodburn et al., 1997, Proc. Am. Assoc. Cancer Res. 38:633). Iressa is an orally active inhibitor which blocks signal transduction pathways implicated in promoting cancer growth (WO02/28409; WO020020; WO02/005791; WO02/002534; WO01/076586; each of which are incorporated herein by reference). Iressa reportedly has antiangiogenic activity, it has antitumor activity against such cancers as colon, breast, ovarian, gastric, non-small lung cancer, pancreatic prostate, and leukemia, it eliminates EGFR, HER2, and HER3 phosphorylation, it inhibits human breast xenograft growth and it has been used in patients (Ciardiello et al. (2001); Moulder et al. (2001); Barker et al. (2001); Moasser et al. (2001); Chan et al. (2002); and Ranson et al. (2002)). Iressa is a quinazoline and has the chemical name 4-quinazolinamine, N-(3-chloro-4-fluorophenyl)-7-methoxy-6-[3-(4-morpholinyl)propoxy]-(9Cl) and the chemical formula C22H24ClFN4O3. The Agent is disclosed in International Patent Application WO 96/33980 (Example 1) has the structure of the formula:

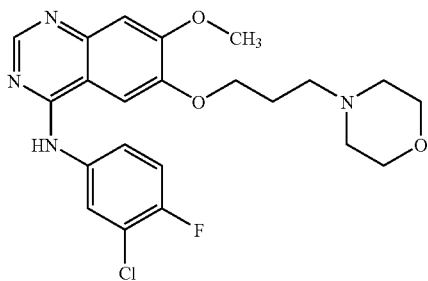

Another specific example of a low molecular weight EGFR antagonist may be the N-[-4-[(3-Chloro-4-fluorophenyl)amino]-7-[3-(4-morpholinyl)propoxy]-6-quinazolinyl]-2-propenamide Dihydrochloride (known as CI-1033 or PD183805 or Canertinib; Pfizer) (Smaill J B. Et al. (1999); Slichenmyer W J et al. (2001)) and has the structure of the formula:

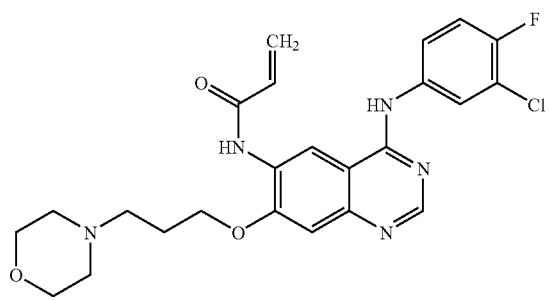

Another suitable low molecular weight EGFR antagonist may be an analog of N-[-4-[(3-Chloro-4-fluorophenyl)amino]-7-[3-(4-morpholinyl)propoxy]-6-quinazolinyl]-2-propenamide Dihydrochloride (CI-1033) known as PD169540 (Pfizer) (Smaill J B. Et al. (2000)).

Another suitable low molecular weight EGFR antagonist may be the 4-[(3-bromophenyl)amino]-6-(methylamino)-pyrido[3,4-d]pyrimidine (known as PD-158780 (Pfizer)) (Rewcastle G W et al. (1998), Cunnick J M et al. (1998)) and has the structure of the formula:

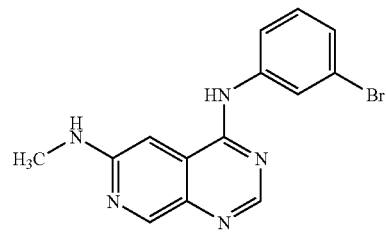

Another suitable low molecular weight EGFR antagonist may be the 4-(3-Chloroanilino)-6,7-dimethoxyquinazoline (known as AG-1478) (University of California)) (Ward W H et al. (1994); U.S. Pat. No. 5,457,105 and European Patent EP 0,566,266). AG-1478 and has the structure of the formula:

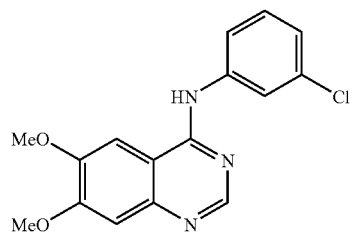

Another suitable low molecular weight EGFR antagonist may be the 4-[(3-Bromophenyl)amino]-6,7-dimethoxyquinazoline hydrochloride (known as PD 153035) (Bridges A J et al. (1996), U.S. Pat. No. 5,457,105 and European Patent 0,566,266) and has the structure of the formula:

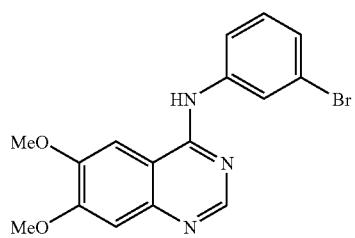

Another suitable low molecular weight EGFR antagonist may be CGP-59326 (Novartis) (Traxler P. et al. (1996)), that has the structure of formula:

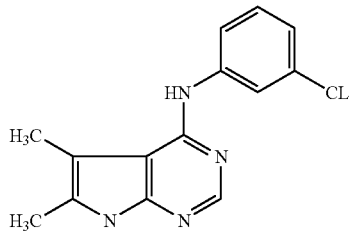

Another suitable low molecular weight EGFR antagonist may be the 4-(R)-phenethylamino-6-(hydroxyl) phenyl-7H-pyrrolo[2,3-d]-pyrimidine (known as PKI-166 (Novartis) (Traxler P et al. (1999)):

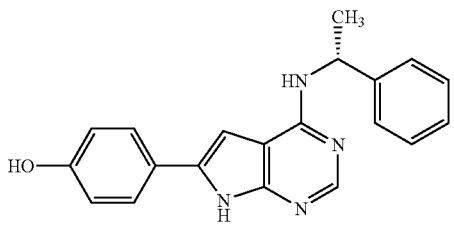

Another suitable low molecular weight EGFR antagonist may be EKB-569 (Wyeth) (Torrance C J. et al. (2000)) that has the structure of formula:

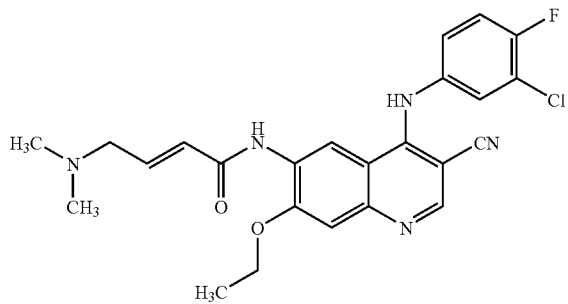

Another suitable low molecular weight EGFR antagonist may be GW-2016 (also known as GW-572016 or lapatinib ditosylate; GSK) (Kim T E et al. (2003)) that has the structure of formula:

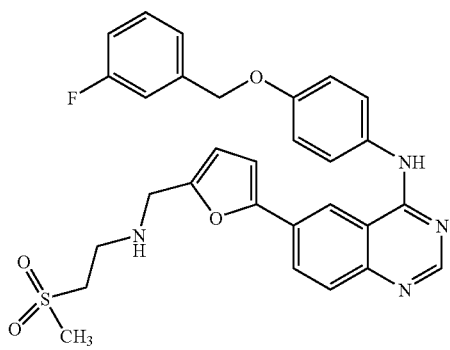

In another embodiment the EGFR antagonist may consist in an antibody or antibody fragment that can partially or completely block EGFR activation by HB-EGF.

Non-limiting examples of antibody-based EGFR antagonists include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR antagonist can be the monoclonal antibody Mab E7.6.3 (Yang, X. D. et al. (1999)), or Mab C225 (ATCC Accession No. HB-8508, U.S. Pat. No. 4,943,533), or an antibody or antibody fragment having the binding specificity thereof. Suitable monoclonal antibody EGFR antagonists include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

In another embodiment, the antagonist of EGFR may consist in a antibody directed against to HB-EGF, in such a way that said antibody impairs the binding of HB-EGF to EGFR. Said antibody can also impairs the activation of EGFR by HB-EGF (Moss M L et al. 1997).

Additional antibody antagonists can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against EGFR, or HE-EGF can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al, 1985, Monoclonal Antibodies and Cancer Therapy, Alan R. Liss, Inc., pp. 77-96). Alternatively, techniques described for the production of single chain antibodies (see, e.g., U.S. Pat. No. 4,946,778) can be adapted to produce anti-EGFR, or anti-HB-EGF single chain antibodies. EGFR antagonists useful in practicing the present invention also include anti-EGFR, or anti-HB-EGF antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to EGFR or HB-EGF.

Humanized anti-EGFR or anti-HB-EGF antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of, the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence The immunized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Another suitable EGFR antagonist may be the cross-reacting material 197 (CRM197), which is a specific inhibitor for the interaction between HB-EGF and HER1 (Mitamura et al., 1995).

Another object of the invention is the use of an inhibitor of EGFR or HB-EGF expression for the manufacture of a medicament intended for treating glomerulonephritis. In a particular embodiment, the invention pertains to the use of an inhibitor of HB-EGF expression.

In one embodiment of the invention, said inhibitor of EGFR or HB-EGF is a siRNA, a ribozyme, or an antisense oligonucleotide Inhibitors of EGFR or HB-EGF expression for use in the present invention may be based on antisense oligonucleotide constructs. Anti-sense oligonucleotides, including anti-sense RNA molecules and anti-sense DNA molecules, would act to directly block the translation of EGFR or HB-EGF mRNA by binding thereto and thus preventing protein translation or increasing mRNA degradation, thus decreasing the level of EGFR or HB-EGF proteins, and thus activity, in a cell. For example, antisense oligonucleotides of at least about 15 bases and complementary to unique regions of the mRNA transcript sequence encoding EGFR or HB-EGF can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of EGFR, or HB-EGF expression for use in the present invention. EGFR or HB-EGF gene expression can be reduced by contacting the tumor, subject or cell with a small double stranded RNA (dsRNA), or a vector or construct causing the production of a small double stranded RNA, such that EGFR or HB-EGF expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of EGFR or HB-EGF expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR or HB-EGF mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of EGFR or HB-EGF expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing EGFR or HB-EGF. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Clifton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Another object of the invention relates to a method for treating glomerulonephritis comprising administering a subject in need thereof with a therapeutically effective amount of an antagonist or inhibitor of expression as above described.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the term "patient" or "patient in need thereof", is intended for a human or non-human mammal affected or likely to be affected with glomerulonephritis.

By a "therapeutically effective amount" of the antagonist or inhibitor of expression as above described is meant a sufficient amount of the antagonist or inhibitor of expression to treat glomerulonephritis at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Screening Methods

Antagonists of the invention can be further identified by the screening methods described in the state of the art. The screening methods of the invention can be carried out according to known methods.

The screening method may measure the binding of a candidate compound to the receptor, or to cells or membranes bearing the receptor, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist or agonist). Further, screening methods may test whether the candidate compound results in a signal generated by an antagonist of the receptor, using detection systems appropriate to cells bearing the receptor. Antagonists can be assayed in the presence of a known agonist (e.g., HB-EGF) and an effect on activation by the agonist by the presence of the candidate compound is observed. Further, screening methods may comprise the steps of mixing a candidate compound with a solution comprising a EGFR, to form a mixture, and measuring the activity in the mixture, and comparing to a control mixture which contains no candidate compound. Competitive binding using known agonist such HB-EGF is also suitable.

Pharmaceutical Compositions

The antagonist or inhibitor of expression of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antagonist or inhibitor of expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The antagonist or inhibitor of expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will further be illustrated in view of the following figures and examples.

FIGURES

FIG. 1: Induction of renal HB-EGF synthesis leads to glomerular activation of EGFR during RPGN. (a) Real time RT-PCR show a 2.5-fold increase in proHB-EGF mRNA expression in renal cortex on day 8 (n>6 per group). (b) Western blot analysis of phosphorylated EGFR to total EGFR ratio in the renal cortex (n=6-8 per group) revealed a 250% increase in EGFR phosphorylation in wild type mice infused with the anti-GBM serum compared to wild type controls. (c) At 8 days, immunostaining for phosphoEGFR was mostly restricted to glomeruli. Genetically determined loss of HB-EGF ((−/−)) was sufficient to prevent EGFR activation in experimental Rapidly progressive glomerulonephritis (RPGN). (b) In a parallel set of experiments, a group of HB-EGF (+/+) animals was treated with intraperitoneal injections of the EGFR inhibitor AG1478 ((+/+)AG) and compared to vehicle-only treated littermates ((+/+)v) to test the potency of in vivo administration of this compound in the renal cortex during experimental RPGN. Data represent the mean±sem. (n=6 per group). * $P<0.05$ versus controls at baseline, ** $P<0.01$ versus controls at baseline. ## $P<0.01$ versus mice treated with vehicle only ((+/+)v).

Figure 2:
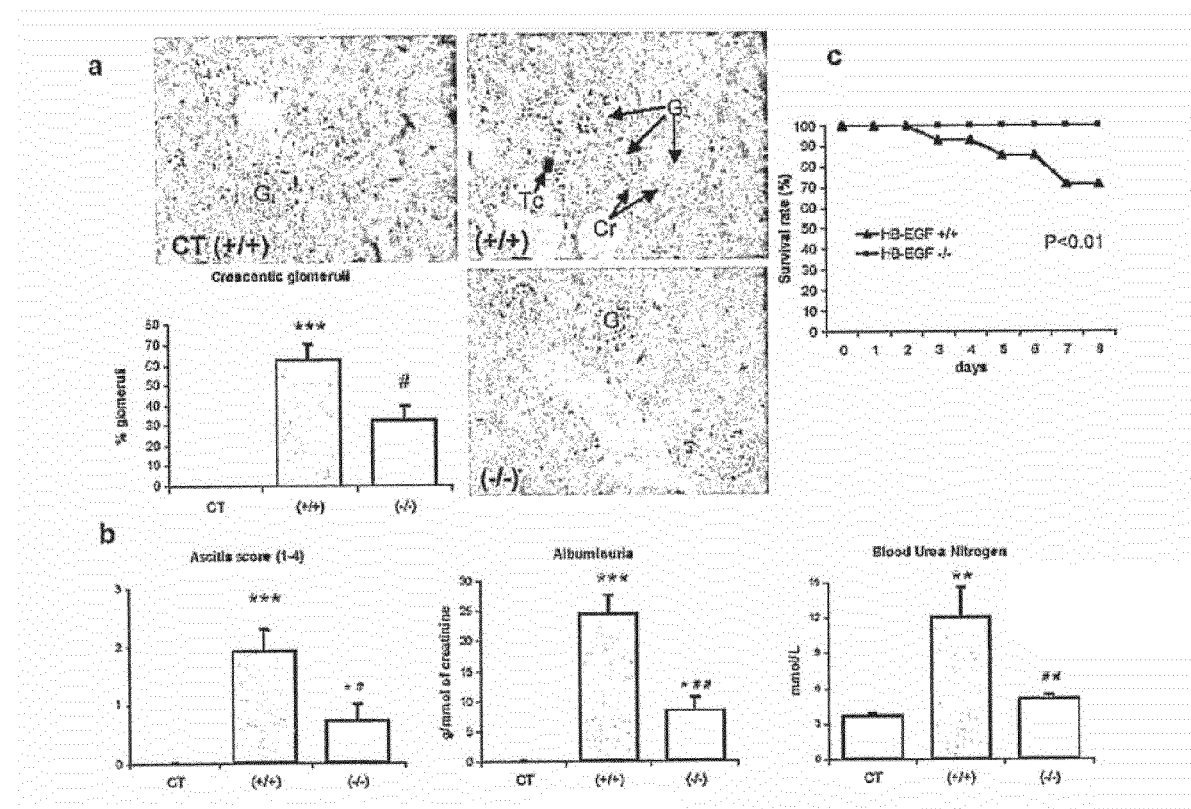

FIG. 2: Deletion of HB-EGF prevents fatal renal destruction. (a) By 8 days after NTS infusion, glomeruli (G) from normal mice display cellular crescents (Cr) and heavy proteinuria leading to packing of tubules with proteinaceous casts (Tc) (upper right panel). The glomeruli from a HB-EGF deficient mouse in the right bottom panel displayed fewer tubular casts and crescentic lesions as presented in the bar graph. (b) Ascites score as an index of albumin plasma loss and water and sodium retention. On day 8 post NTS, most wild type animals displayed weight gain along with obvious ascites (more than 1 mL). (c) ELISA for quantitative determination of albumin in mouse urine. Experimental RPGN provoked marked albuminuria compared to undetectable levels in either HB-EGF (−/−) or HB-EGF (+/+) controls (CT) at baseline. Albuminuria normalized to creatininuria was threefold less in HB-EGF (−/−) animals than in their HB-EGF (+/+) counterparts. Serum urea concentrations indicate renal failure and increased fourfold by 8 days of RPGN in HB-EGF (+/+) animals compared to unchallenged controls and also to NTS-challenged HB-EGF (−/−). Data represent the mean±sem. (n=9-12 per group). * $P<0.05$ versus controls at baseline,  $P<0.01$ versus baseline, * $P<0.001$ versus baseline. # $P<0.05$ versus NTS-treated (+/+), ## $P<0.01$ versus NTS-treated (+/+). (c) Survival curve for challenged HB-EGF (+/+) and HB-EGF (−/−) mice. In all cases, death was associated with extreme renal damage with macroscopic hematuria (blood leakage in the urine) and animals succumbed from renal failure.

Figure 3:
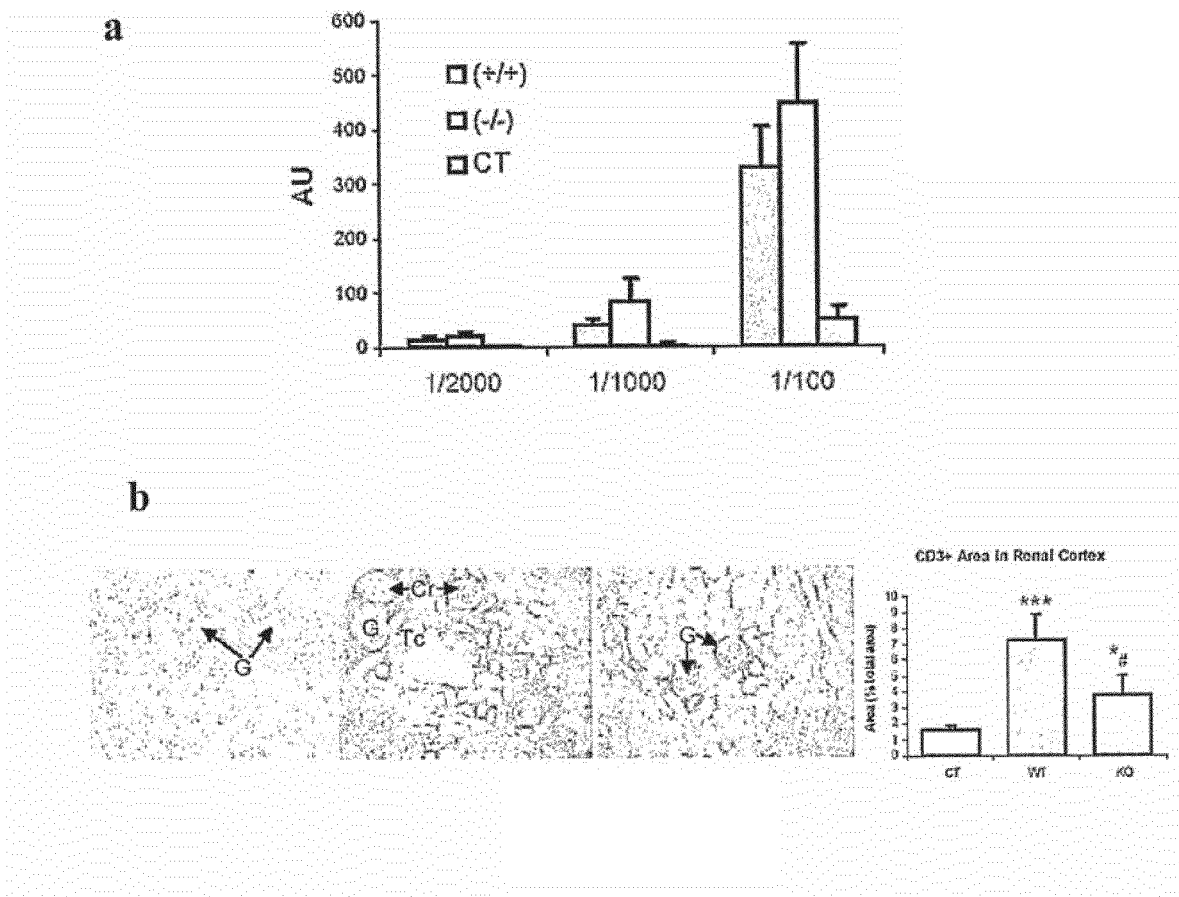

FIG. 3 (a) Mouse IgG anti-sheep IgG were detected in an ELISA. Serial dilutions of plasma from immunized HB-EGF (−/−) and HB-EGF (+/+) mice with sheep IgG showed similar markedly increased antibody titers in both groups comapered to non immunized normal mice (CT). AU: arbitrary unit of optical density induced by peroxidase-associated activity. (b) By comparison with normal mice at baseline (CT), immunostaining for CD3+ cells shows marked influx of T cells around the Bowman capsule, surrounding the most affected glomeruli with epithelial crescents (Cr) during the course of NTS-induced RPGN. T lymphocytes infiltrates extend within the renal interstitium beyond glomeruli. Image analysis confirmed a four to fivefold increase in the renal cortex area occupied by CD3 expressing cells in wild type (WT) HB-EGF (+/+) animals on day 8 that was significantly blunted in HB-EGF gene knock out mice. Data represent the mean±sem. (n=12 per group). * $P<0.05$ versus baseline, *** $P<0.001$ versus baseline. # $P<0.05$ versus wild-type HB-EGF (+/+) group.

Figure 4:
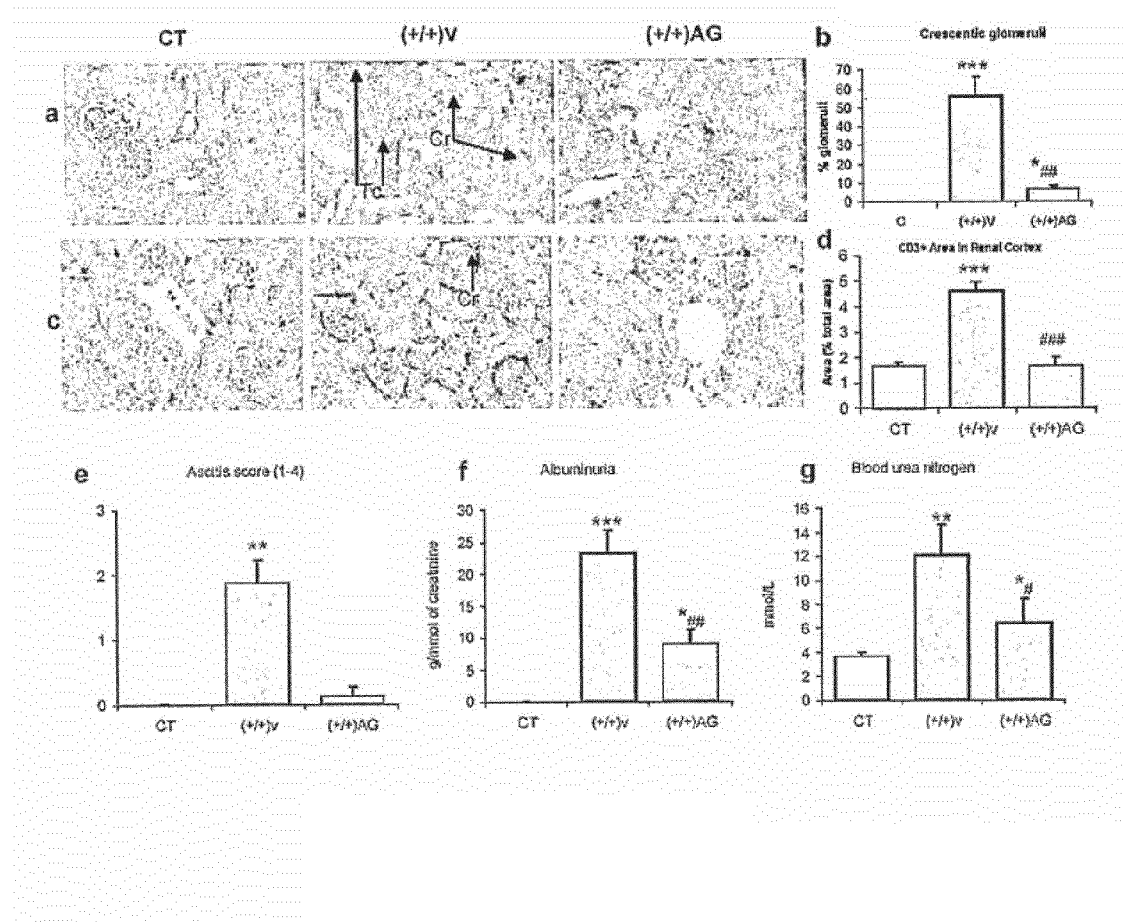

FIG. 4: Effect of EGFR tyrosine kinase inhibitor AG1478 on severity of RPGN. Twelve hours prior to intravenous injection of anti-GBM nephrotoxic serum, wild type (+/+) male mice were treated with 100 μl of a saline solution with 1% carboxymethylcellulose and 10% DMSO with ((+/+)AG) or without ((+/+)v) 30 mg per kg body weight of AG1478 (i.p.).

On day 8, mice were killed and comparison were performed with morphological (Masson trichrome staining, count of crescentic glomeruli, staining for CD3 positive cells) (a-d) and functional indexes (ascites, albuminuria, blood urea nitrogen) (e-g). Data represent the mean±sem. (n=6 mice per group). * $P<0.05$ versus controls at baseline (CT),  $P<0.01$ versus CT, * $P<0.001$ versus CT. # $P<0.05$ versus (+/+)v, ## $P<0.01$ versus (+/+)v, ## $P<0.001$ versus (+/+)v. (a-d) AG1478 reduces crescent formation and T cells infiltrates in vivo. (e-g) AG1478 prevents albumin urinary leakage and renal failure.

Figure 5:
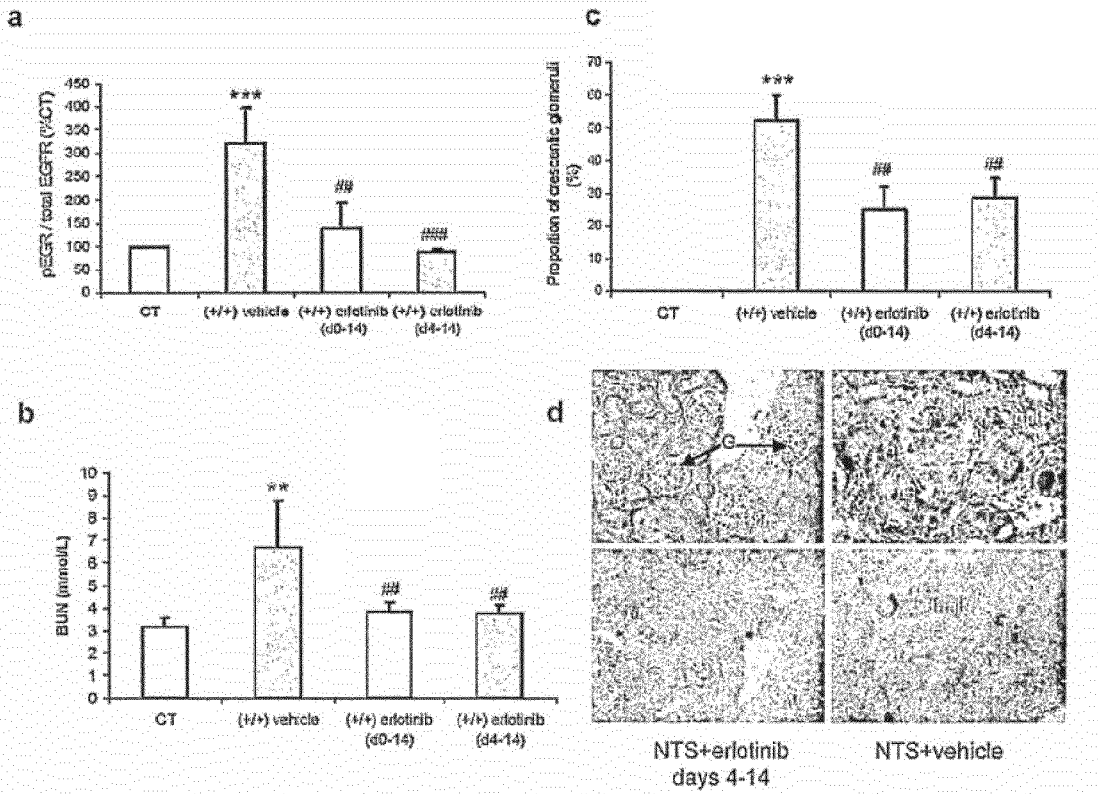

FIG. 5: Effects of the clinically developed EGFR inhibitor erlotinib administered either in preventive protocol or in a curative protocol, starting twelve hours prior administration of anti-GBM serum (d0-14) or four days later (d4-14), respectively. These two groups were compared to littermate male mice that were treated with vehicle only ((+/+)vehicle) or to unchallenged mice (CT). Mice were sacrificed after 14 days of RPGN. In any case, erlotinib blocked phosphorylation of EGFR in the renal cortex (a), prevented renal failure with normal blood urea nitrogen levels (b), blunted or stopped the development of glomerular injury (c). Data are mean±sem, (n=9 mice per group).  $P<0.01$ versus controls at baseline (CT), * $P<0.001$ versus CT, ## $P<0.01$ versus (+/+)vehicle, ## $P<0.001$ versus (+/+)vehicle. (d) Masson trichrome staining of renal cortex from a mouse treated with erlotinib (left panel) and a vehicle-treated mouse (right panel). On day 14, delayed EGFR inhibition from day 4 to day 14 had blunted necrotic glomerular lesions (Ne), cellular crescents (Cr), tubular proteinaceous casts (Tc) and diffuse CD3 positive cells infiltrates (Infilt) seen in untreated mice with RPGN. Original magnification, ×400 (upper panels) and ×200 (lower panels).

Figure 6:
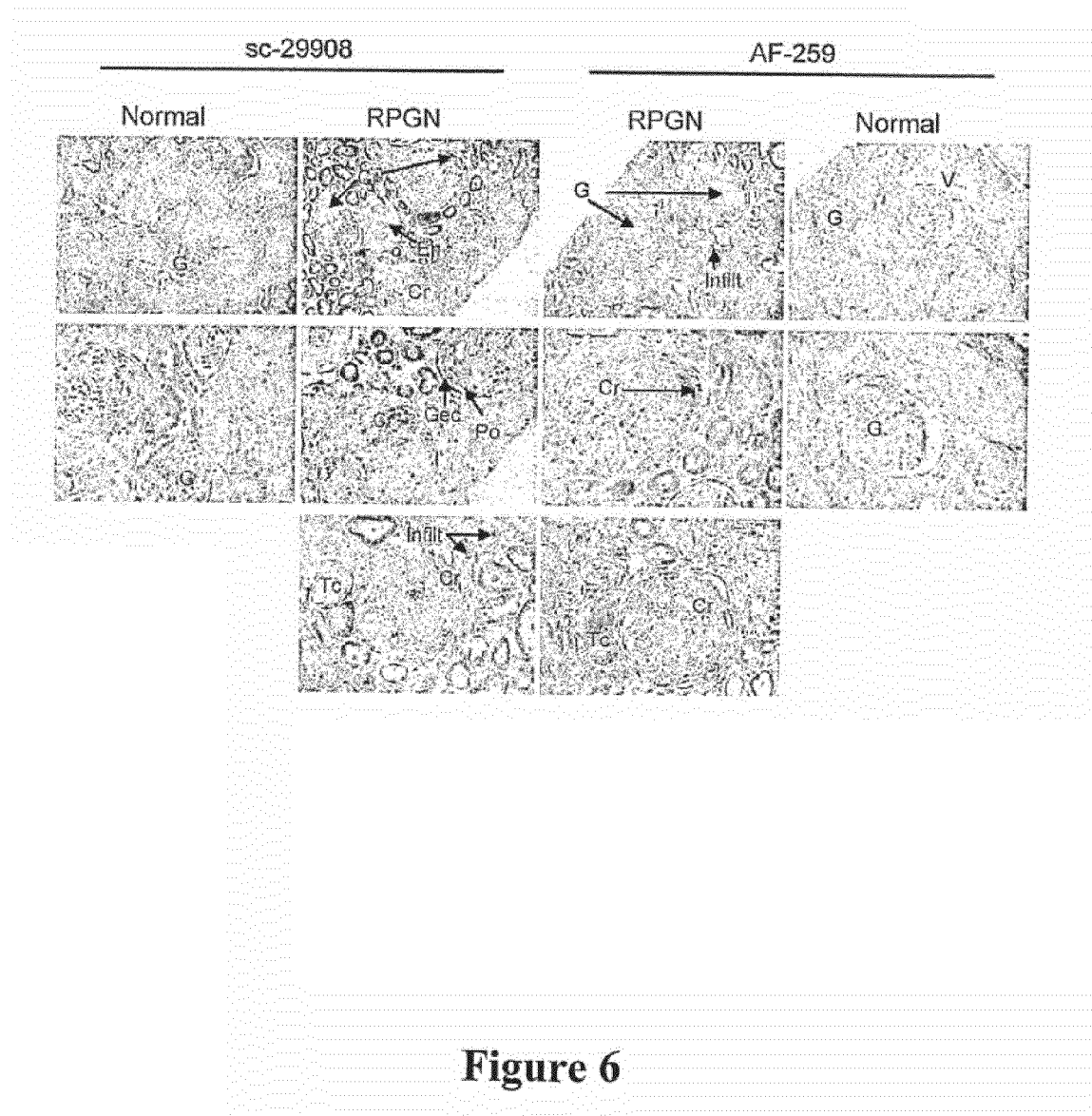

FIG. 6: High de novo expression of HB-EGF in glomeruli is a feature of human crescentic RPGN. Immunostaining for HB-EGF using two unrelated antibodies (sc-29908 and AF-259) demonstrates faint tubular and vascular expression of HB-EGF in normal human kidneys. By contrast, biopsies from patients with RPGN displayed strong immunolabeling for HB-EGF within cellular crescents (Cr). Moreover, at the edge of crescents, glomerular epithelial cells of the Bowman capsule (Gec) and podocytes (Po) focally express HB-EGF. Some tubules sections, interstitial mononuclear infiltrating cells (Infilt) and endothelial cells (En) also display enhanced staining. Tc: tubular proteinaceous cast, V: vascular smooth muscle cells. Bottom middle panels: comparison of immunostaining for HB-EGF with sc-29908 and AF-259 on serial sections of the same renal biopsy, demonstrating the similar staining pattern in the crescent (Cr). Original magnification: ×200 (upper panels); ×400 (middle and lower panels).

EXAMPLE

Materials and Methods:

Animals: Male mice used were HBEGF gene deficient mice (HB-EGF−/−) and their controls (WT). HB-EGF −/− mice were obtained on a mixed C57BL/6J×129 background by homologous recombination, HB-EGF exons 1 and 2 being replaced with PGK-Neo, as previously reported (Jackson L F. et al. 2003).

Induction of crescentic glomerulonephritis: The accelerated anti-GBM model was used, as previously described (Topham P S. et al. 1999, Lloyd C M. et al. 1997). Briefly, WT and HB-EGF−/− mice received subcutaneous injection with 200 μg normal sheep IgG (100 μl in each flank of normal sheep IgG (Sigma) diluted to 1 mg/ml in a solution of 50% freund complete adjuvent and 50% saline). Six days later (day 1), glomerulonephritis (GN) was induced by intravenous injection of 50 μl sheep anti-glomerular basement membrane (GBM) serum diluted to 7 mg/ml in saline. Serum injection was repeated twice (days 2 and 3), with serum dilution increased to 70 mg/ml. On days 0, 1, 2, 3, 5 and 7, mice received intraperitoneal injection of either AG1478 (LC Laboratories), a pharmacological inhibitor of EGFR tyrosine kinase activity (30 mg.kg-1.day-1 in 100 μl of a saline solution with 1% carboxymethylcellulose (CMC) and 10% DMSO), or 100 μl of saline solution with 1% CMC and 10% DMSO as control. On day 8, mice were sacrified after body weight measurement and 12 hours urines collection with metabolic cages. In another set of experiments, two groups of mice received erlotinib (100 mg.kg-1.day-1 per gavage in 100 μL of saline and 1% CMC solution). Erlotinib was started either either on day 0 similarly to the protocol with AG1478, or on day 4 after anti-GBM serum injection, at the peak of albumiunuria and acute renal failure. These two groups were compared to vehicle-treated animals (n=9 per group). On day 14, mice were sacrified. Blood was obtained from mice by aortic catheterization. Kidneys from each mouse were processed for immunohistochemistry, protein and mRNA analysis, and the remaining half-kidney fixed in 10% neutral-buffered formalin for histological study. All animal experiments were conducted in accordance with the French guidelines from the Ministry of Food and Agriculture for care and use of laboratory animals.

Assessment of ascitis, renal function and albuminuria: Ascitis was quantified with a 5 scale score (0-4) the day of sacrifice by examinining the peritoneum and collection of peritoneal liquid with a syringe and a 30G needle, as follow: 0: no asciitis, 1: discrete liquid rention seen between intestinal loops, not punctionnable or less than 1000 μL, 2: at least 1000 μL of ascite collected, 3: 1000 to 1500 μL collected, 4: more than 1.5 mL collected. Stage 2 to 4 were associated with clinically evident ascitis and weight gain before sacrifice.

Serum and urinary creatinine, and blood urea nitrogen (BUN) were quantified spectrophotometrically using a colorimetric method. Urinary albumin excretion was measured using a specific ELISA assay for quantitative determination of albumin inmouse urine (CellTrend GmbH).

Histopathological study: For light microscopy, half a mouse kidney was fixed and embedded in paraffin, and 3 μm thick sections were, performed. Histopathological changes were evaluated using Masson's trichrome coloration by an examiner who was masked to the experimental conditions. The proportion of crescentic glomeruli was determined by examination of at least 80 glomeruli per section.

Immunohistochemistry was performed using an automated slide stainer (Ventana NexES IHC Staining System). Paraffin-embedded sections were stained for macrophages using rabbit anti-F4/80 (MCA497B, Serotec) diluted 1:50, and T lymphocytes using rabbit anti-CD3e (Dako) diluted 1:200.

For immunofluorescence in mouse tissues, cryostat sections of 4 μm were immediately fixed in acetone, washed in PBS and then incubated with antibodies in a humid incubator. Deposits of mouse IgG in kidney were evaluated using FITC rat anti-mouse IgG (FI2000, Vector) (1:100 dilution, incubation for 1 hour at room temperature). The phosphorylation of EGFR was assessed using a rabbit anti phospho-EGFR (anti-Tyr1068, Cell Signaling) (1:400 dilution, incubation overnight at 4° C.) and revealed with an anti-rabbit Texas Red-conjugated antibody (111-075-003, Jackson Immunoresearch) (1:200 dilution, incubation for 1 hour at room temperature).

Pro-HB-EGF expression was assessed by immunohistochemistry in normal human kidneys and biopsies from patients with crescentic Rapidly progressive glomerulonephritis (RPGN). Formalin-fixed sections were incubated with two distinct antibodies, either rabbit anti-human HB-EGF (Santa Cruz Biotechnologies, sc 28908) or goat anti-human HB-EGF (R&D Systems, AF-259-NA). Following overnight incubation at 4° C. at the recommend dilutions and washes, specific staining was revealed using Histofine staining reagents (Nichirei Biosciences).

Assessment of serum anti-sheep IgG titers: Anti-sheep IgG titers in serum were determined by ELISA assay. Plaques were coated with 20 μg/ml sheep IgG (Sigma) overnight at 4° C., and then blocked using a 5% albumin solution. Serum to be tested was added into wells at different dilutions ranging from 1:100 to 1:2,000. Peroxidase-coupled anti-mouse IgG (Rockland) and peroxidase substrate were successively added. Anti-sheep IgG titers were determined spectrophotometrically using a calibration curve established with a range of diluted mouse IgG.

Western blot analysis: Proteins were extracted from kidneys using a lysis buffer (Phosphosafe extraction buffer, Novagen) and quantified according to Bradford's method. 50 μg of proteins migrated into a NuPAGE 4/12% electrophoresis gel (Invitrogen), secondarily transferred to PVDF membranes. Immunoblotting was performed using the rabbit anti phospho-EGFR (Cell Signaling) diluted 1:1,000 or a rabbit anti-EGFR diluted 1:5,000 (Cell Signaling) as control for lane loading. Then, horseradish peroxidase-linked donkey secondary antibody (Amersham Pharmacia Biotech) diluted 1:2,000 was added and revelation was subsequently made using ECL plus kit (Amersham Pharmacia Biotech) on autoradiography film, followed by densitometric analysis.

Semi-quantitative Reverse Transcriptase Polymerase Chain Reaction (RT-PCR) analysis: Total RNA was extracted from renal cortex using TRIzol solution (Gibco BRL) and methyl trichloride. RNA quality was checked by control of optical density at 260 and 280 nm, and by electrophoresis. cDNA was reverse-transcribed from 1 μg RNA by using a reverse transcriptase (Superscript II, Gibco BRL), then amplified in a thermocycler (ABI Prism 7000) for 40 cycles in a mix containing DNA polymerase and SYBR Green (Quantitect SYBR Green PCR kit, Qiagen). A cycle profile consisted of: 95° C. for 45 sec and 60° C. for 1 min for annealing and primers extension.

Primers were for: HB-EGF (5'-TTCCCAGACAGGATCT-CACC-3' and 5'-GTGGGTAGCAGCTGGTTTGT-3') and for 18S: (5'-GAGCGAAAGCATTTGCCAAG-3' and 5'-GGCATCGTTTATGGTCGGAA-3') for normalization. Normal renal cortex cDNA was used as reference to establish calibration curves of HB-EGF and 18S cycle threshold (CT). Results are expressed as the HB-EGF/18S cDNA ratio.

Statistical analysis: Data were expressed as mean+SEM. Comparison between groups were analysed by Mann-Whitney U test, or ANOVA for experiments with more than 2 subgroups followed by protected least significance difference Fisher's test. Values of $P<0.05$ were considered significant. All analyses were performed with Statview software (SAS Institute Inc.).

Results:

Activation of proHB-EGF gene during crescentic glomerulonephritis: Expression of the proHB-EGF mRNA was studied by real-time RT-PCR in kidneys harvested 8 days after anti-glomerular basement membrane nephrotoxic serum (NTS) injection in normal mice (+/+). ProHB-EGF mRNA expression was then 3-fold increased (cDNA proHB- EGF/cDNA 18S ratio 3.5±1.4 and 10.8±1.7 respectively for immunized mice vs. non immunized mice, n=6, P<0.05) (FIG. 1a).

Activation of EGFR tyrosine kinase during crescentic glomerulonephritis: The HB-EGF binds to and activates both the EGFR/ErbB and the ErbB4. Subsequently, we studied the phosphorylation of EGFR in the process of crescentic glomerulonephritis, using immunoblot analysis of phospho-EGFR (pEGFR) in lysates extracted from renal cortex 8 days after the beginning of experimental crescentic glomerulonephritis (FIG. 1b). By comparison with non immunized HB-EGF (+/+) or HB-EGF (−/−) controls, phosphorylation of EGFR was highly induced after NTS (pEFGR/EGFR ratio 262±65% of baseline controls (CT), n=6, P<0.01 vs. CT). This activation of EGFR was localized by immunofuorescence, showing a strong signal in the glomeruli with pEGFR specific staining that was markedly intense in cells of the glomerular capillary wall and in mesangial cells. We demonstrated the specificity of EGFR phosphorylation in vivo in immunized mice which were daily injected with the EGFR tyrosine kinase inhibitor AG1478 (AG) or vehicle alone (v). In this experiment, the phosphorylation of EGFR assessed by western blotting and by immunofluorescence in the renal cortex of AG-treated animals was markedly blunted by nearly 9-fold on day 8 post NTS (pEFGR/EGFR ratio 11% of vehicle only-treated mice, n=6, P<0.01), and consistently, faint or no signal was detectable in AG1478-treated glomeruli (FIG. 1b and FIG. 1c).

Interestingly, EGFR was not highly phosphorylated in the renal cortex of HB-EGF deficient mice after injection of NTS (pEGFR/EGFR ratio 71±5% of baseline CT, n=6, NS vs. CT, P<0.01 vs. HB-EGF (+/+), suggesting a predominant role for HB-EGF in EGFR activation in crescentic glomerulonephritis (FIG. 1b and FIG. 1c).

HB-EGF (−/−) mice develop attenuated crescentic glomerulonephritis and are protected from lethal acute renal failure: 12 HB-EGF (−/−) and 14 HB-EGF (+/+) male littermates had similar renal histology and functional parameters (μalbuminuria, serum creatinine and BUN) at baseline. Therefore, subsequently shown controls (CT) are pre-immunized unchallenged HB-EGF (+/+) normal mice at baseline unless specified.

HB-EGF (+/+) mice injected with NTS developed severe glomerulonephritis characterized by crescent formation by day 8 (crescentic glomeruli ratio: 70±8% vs 0% in (+/+)/NTS vs. (+/+) or (−/−) CT respectively, P<0.01) (FIG. 2a). HB-EGF (−/−) mice developed attenuated renal damages since histological examination revealed less crescent formation (32.2±7.3% of the glomeruli, P<0.05 vs. (+/+)). HB-EGF deficiency also prevented the development of symptoms of severe nephritic syndrome with a milder incidence and importance of ascitis in HB-EGF (−/−) than in HB-EGF (+/+) mice (0.8±0.2 vs. 1.9±0.2, P<0.05) (FIG. 2b) and was associated with significantly less functional renal alterations with fewer albuminuria (8.3±2.2 vs. 24.4±4.0 g/mmol creatinine, P<0.01) in HB-EGF (−/−) mice than in HB-EGF (+/+). Whereas HB-EGF (+/+) developed rapid renal failure, HB-EGF (−/−) exhibited BUN levels within normal ranges (BUN values: 12.1±2.5 mM, 5.1±0.4 mM and 3.6±0.3 mM for (+/+) and (−/−) after NTS and controls at baseline, respectively, P<0.01). In line with the renal protection associated with the lack of HB-EGF, HB-EGF −/− animals survived whereas 30% of normal mice died within 8 days (P<0.01, FIG. 2c) with nearly 100% of crescentic glomeruli and terminal renal failure.

Role of HB-EGF in the immuno-inflammatory response associated with crescentic glomerulonephritis: Although a critical role of T cells and macrophages has been demonstrated in this model as well as in human crescentic Rapidly progressive glomerulonephritis (RPGN) (Neale T J. et al., 1988; Lloyd C M. et al. 1997; Hancock W W. et al., 1984) immune complexes may play a pathophysiological role at the very early steps of the disease, promoting activation of complement (Neale T J. et al., 1988; Lin F. et al. 2004). Therefore we assessed the magnitude of the humoral response to sheep IgG of HB-EGF −/− and +/+littermates. Serial dilutions of serums from preimmunized animals showed similar titers of mouse anti-sheep antibodies (FIG. 3a) with similar pattern of IgG deposition in glomerular basement membranes in the kidneys, suggesting no role of HB-EGF in the humoral immune response. By contrast, HB-EGF deficient mice displayed fewer CD3 positive T cells infiltrates within and around the glomeruli than their wild type counterparts following NTS administration (P<0.05) (FIG. 3b). Similarly, HB-EGF −/− animals displayed less F4/80 positive macrophages in the kidney cortex than wild type mice at day 8 after NTS.

Pharmacological blockade of the EGFR tyrosine kinase prevents crescentic glomerulonephritis, renal failure: In the model of RPGN, crescents formation was accompanied by marked induction of EGFR phosphorylation within glomeruli and enhanced expression of proHB-EGF mRNA in the kidney cortex. Moreover, HB-EGF-deficient mice appeared to be partially and significantly protected against renal lesions, and did not display high levels of EGFR phosphorylation. Taken together, these results suggested that HB-EGF-dependent activation of the EGFR is a prerequisite for crescent formation, albuminuria and renal failure. Thus, we tested the proof of concept that pharmacological inhibition of the EGFR pathway may halt renal damage.

AG1478 is a synthetic inhibitor of EGFR autophosphorylation (Osherov N. et al. 1994). Daily peritoneal administration of AG1478 in wild type mice (+/+)AG prevented the phosphorylation of EGFR observed in animals receiving the vehicle only (+/+)v (FIG. 1b). Furthermore, AG1478 administration dramatically reduced the development of renal lesions (FIG. 4). Almost all glomeruli were normal on day 8 after induction of RPGN in AG1478-treated animals (% of crescentic glomeruli: 6.8±1.7% vs. 55.7±10.1% for (+/+)AG and (+/+)v groups respectively, n=6, P<0.01) (FIG. 4a,b). Again, increased periglomerular and interstitial CD3+ cell infiltrates were absent in AG1478-treated animals (P<0.001 vs. vehicle-treated animals) since CD3+ cells area remained spectacularly normal (FIG. 4c,d). These histopathological observations were associated with lower incidence and severity of asciitis (FIG. 4e) and confirmed by biochemical markers, since in EGFR inhibited animals, albuminuria was significantly lower than in vehicle only-treated mice (8.9±2.3 vs. 23.2±3.4 g/mmol creatinine for (+/+)AG and (+/+)v respectively, n=6 P<0.01) (FIG. 4f) and renal function was preserved (BUN: 6.39±2.0 vs. 23.2±3.4 and 3.6±0.3 for (+/+) AG, (+/+)V and CT respectively, n=6 per group, P<0.05 for (+/+)AG vs. (+/+)V and p=NS for (+/+)AG vs. CT) (FIG. 4g). Finally, we observed that no AG1478-treated HB-EGF(+/+) mice died within 8 days of RPGN.

Delayed pharmacological blockade of the EGFR tyrosine kinase stops crescentic glomerulonephritis and prevent renal failure: To determine whether inhibition of the EGFR pathway may be a therapeutic option in RPGN, we administered a commercially available EGFR inhibitor, erlotinib, on day 4 after infusion of anti-GBM serum. This time point was chosen because it is when albuminuria and acute renal peak at their maximum, a situation that is relevant to clinical challenges. This regimen was compared to the effect of vehicle alone and to the administration of erlotinib 12 hours prior to the first infusion of anti-GBM serum. In any case, the chosen dose of erlotinib was significantly effective to inhibit EGFR phosphorylation on day 14 upon experimental RPGN (FIG. 5a). Again, "preventive" EGFR tyrosine kinase inhibition blunted the proportion of crescentic glomeruli (25.0±6.9 vs. 53.0±7.7° A), for erlotinib-treated group and vehicle only-treated group; P<0.01) (FIG. 5b), the rise in serum creatinine (1.4±0.1 vs. 1.8±0.2 mmol/L; P<0.05) and blood urea nitrogen (3.8±0.4 vs. 6.7±2.0 mmol/L; P<0.01) (FIG. 5c). More interesting were the experimental therapeutic actions of delayed erlotinib administration on renal damages, cell infiltrates and renal failure (FIG. 5b,c,d).

High expression of HB-EGF in human kidneys with RPGN: To determine whether upregulation of HB-EGF also occur in glomeruli of individuals with crescentic RPGN, we performed immunostaining with two unrelated antibodies to human HB-EGF (FIG. 6). Staining with these two antibodies showed a similar pattern of HB-EGF expression in normal human kidney as well as in renal biopsies from patients with RPGN. Notably, we found a marked increase in HB-EGF in glomeruli from patients with crescentic RPGN whereas normal human kidneys showed low level of expression that was restricted to tubules. Up-regulated expression of HB-EGF was mainly observed in glomerular epithelial cells (GECs), cells of Bowman's capsule, proximal and distal tubules. Moreover, HB-EGF staining was more intense and diffuse in glomeruli with crescents than seen in less affected glomeruli within the same tissue sample. Weaker but consistent HB-EGF expression was also observed in mesangial and arterial smooth muscle cells.

Discussion:

We hypothesized that HB-EGF could be induced in the kidney, activate EGFR tyrosine kinase activity and promote glomerular inflammation, damage and renal failure in a murine model of RPGN. Up-regulation of HB-EGF in glomeruli has been reported a rat model of diabetic nephropathy (Lee Y J. et al. 1995), and prior the onset of proteinuria in experimental rat models of membranous and minimal change nephropathy (Paizis K. et al. 1998). Meanwhile, it is unknown whether EGFR phosphorylation was induced in these models and whether HB-EGF could exert any pathophysiological actions. In the puromycin aminonucleoside nephritis rat model, administration of affinity-purified monoclonal antibody to human HB-EGF induced earlier onset of albuminuria with no subsequent actions on renal function and other major renal end-points. In this particular model, HB-EGF expression was selectively induced in podocytes and seemed to promote survival of these cells (Khong T F. et al, 2000). Therefore, we looked at a more severe model of renal damage with inflammatory processes such as seen in human proliferative glomerulonephritis. Crescentic RPGN are the most severe class of glomerulopathies in humans and require costly and side-effects prone immunosuppressive therapies (Levy J B. et al. 2001; Salama A D. et al. 2001). Glomerular and interstitial hypercellularity are the earliest abnormalities in our model of accelerated nephrotoxic serum nephritis (Lloyd C M. et al. 1997; Topham P S. et al. 1999), and they occur concomitantly with the appearance of severe proteinuria and transient acute renal failure. The inflammatory infiltrate in glomeruli and interstitium is composed of T-lymphocytes, mononuclear phagocytes and neutrophils (Lloyd C M. et al. 1997; Topham P S. et al. 1999), much as has been described in other animal models of crescentic glomerulonephritis and human RPGN (Tipping P G. et al. 2003; Hancock W W. et al. 1984; Ng Y Y. et al. 1999; Nikolic-Paterson D J. et al. 2001; Boucher A. et al. 1987; Kalluri R. et al. 1997; Guettier C. et al. 1986; Levy J B. et al. 2003). Interestingly, HB-EGF is rapidly expressed in mesangial cells and glomerular epithelial cells in the anti-Thy-1 Ab model of mesangial injury (Polihronis M. et al. 1996) and Feng et al. have reported an induction of HB-EGF mRNA expression in glomeruli 30 minutes upon anti-GBM Ab administration in rats (Feng L. et al. 2001). Interestingly in this latter study, neutralisation of HB-EGF with an Ab prevented the fall in glomerular filtration rate (GFR) and single nephron GFR (SNGFR) but did not influence the changes in glomerular inflammatory response to the anti-GBM serum. However, this elegant work was a short-term study with no assessment of clinically relevant end-point such as renal damages, proteinuria and death. In this model, upregulation of HB-EGF decreased spontaneously after 3 hours and reverted to baseline within 6 to 24 hours. In a more severe model of accelerated crescentic glomerulonephritis, a marked and sustained increase in HB-EGF mRNA renal expression at day 8 up to 21 days was reported (Feng L. et al. 2000). Consistently, a clinical report of high mesangial expression of HB-EGF in a variety of human proliferative and non proliferative glomeronephritis also suggests that HB-EGF may be chronically induced in renal diseases (Takemura T. et al. 1999). Sustained expression of HB-EGF in myofibroblasts during remodeling of the peri-infarct region of the remnant kidney model has also been reported (Kirkland G. et al. 1998). However, in our model of dramatic glomerular injury, because HB-EGF deficiency or EGFR blockade prevented the development of asciitis and renal leukocytic infiltrates prior the appearance of patent crescentic proliferative lesions and interstitial fibrosis, we suggest that the HB-EGF-EGFR pathway is effective at very early time points in promoting renal damage. Several other cell types may participate to early HB-EGF release. HB-EGF was reported in wound fluid (Marikovsky M. et al. 1993) with high concentrations in conditioned medium of macrophages and macrophage-like U-937 cells (Higashiyama S. et al. 1991). HB-EGF has also been observed in T-cells subsets in vitro and in tumors and atherosclerotic plaques (Blotnick S. et al. 1994; Topham P S. et al. 1999), although with no known functions so far. The intensity of HB-EGF expression within interstitial inflammatory infiltrates was uneven and much weaker than the expression of HB-EGF within crescentic glomeruli in mouse and human kidney cortex. Accordingly, immunolocalization of phosphorylated EGFR revealed a pattern restricted to the glomeruli. Although these results do not rule out a role for the HB-EGF/EGFR pathway in the early inflammatory phase of the disease, they suggest a prominent pathophysiological action of HB-EGF released by intrinsic renal cells, likely upon stimulation by immune mediators.

To our knowledge, the present study is the first report that demonstrate a pathophysiological role of HB-EGF in a model of human disease and a role of EGFR in a model of renal immune-mediated destruction. The use of a mouse genetic model of HB-EGF deficiency allowed us to overcome the issues of specificity, affinity and bioavailability of neutralizing antibodies. Moreover, although HB-EGF is known has a growth factor, it appears that its observed actions exceed its known mitogenic properties since HB-EGF deficient mice were protected from inflammatory renal infiltrate and albuminuria prior to the development of marked renal cell proliferation. To ascertain that these effects were not due to a developmental action of chronic HB-EGF deficiency on the maturation of the immune system or of the kidney, we verified that inhibition of the EGFR, the main receptor for HB-EGF, would mimic the phenotype induced by genetic targeting of the HB-EGF gene. In addition, this experiment allowed to verify the involvement of EGFR/ErbB1 that proved to be highly activated in diseased glomeruli, suggesting that activation of ErbB4, another receptor for HB-EGF that may promote distinct cellular effects (Elenius K. et al. 1997), plays a marginal pathophysiological role if any. Third, EGFR was not highly phosphorylated in the renal cortex of HB-EGF deficient mice after injection of NTS, which suggests a predominant role for HB-EGF in EGFR activation in RPGN but cannot rule out the participation of other ligands of minor importance. In this regard, AG1478 was more effective in preventing cell infiltrate than HB-EGF deficiency. Fourth, the efficiency of two distinct EGFR inhibitors administrated either shortly prior anti-GBM serum infusion or 4 days after the beginning of the RPGN, (ie: after the period of pre-immunization); suggests that recruitment of the HB-EGF-EGFR pathway is involved during the effector phase of the disease and does not play a significant role in the pre-immunization process. Accordingly, the humoral response was similar in HB-EGF deficient and normal animals that exhibited similar levels of anti-sheep IgG.

Finally, we observed a consistent up-regulation of HB-EGF protein expression in glomeruli from human kidneys with crescentic RPGN compared to a low constitutive tubular expression in normal tissues as previously described (Nakamura Y. et al., 2001). Expression of HB-EGF was mainly observed in glomerular epithelial cells (GECs), cells of Bowman's capsule and distal tubules, a pattern close to the one reported in a rat model of focal adhesive glomerular sclerosis induced by puromycin aminonucleoside (Paizis K. et al. 1999). Interestingly, within the same renal biopsy, the most severely affected glomeruli displayed the most intense staining to HB-EGF, again suggesting a pathophysiological role for HB-EGF in human RPGN.

In conclusion, these data provide evidence for the concept that immune-mediated glomerular injury leads to active and sustained pathophysiological recruitment of glomerular EGFR by HB-EGF. After the momentum deduced from prior studies suggesting a protective or a negligible role for HB-EGF in models of mild glomerular injury (Feng L. et al. 2000; Khong T F. et al. 2000), activation of EGFR is here demonstrated to be involved in renal inflammation, glomerular destruction and renal failure. The therapeutic potential of specific EGFR inhibitors may be envisioned in crescentic and other inflammatory glomerulonephritis.

REFERENCES

Al-Obeidi F A, Lam K S. Development of inhibitors for protein tyrosine kinases. Oncogene. 2000 Nov. 20; 19(49):5690-701.

Asakura, M., Kitakaze, M., Takashima, S., Liao, Y., Ishikura, F., Yoshinaka, T., Ohmoto, H., Node, K., Yoshino, K., Ishiguro, H., Asanuma, H., Sanada, S., Matsumura, Y., Takeda, H., Beppu, S., Tada, M., Hari, M., and Higashiyama, S. 2002. Cardiac hypertrophy is inhibited by antagonism of ADAM12 processing of HB-EGF: metalloproteinase inhibitors as a new therapy. Nat. Med., 8: 35-40.

Barker A J, Gibson K H, Grundy W, Godfrey A A, Barlow J J, Healy M P, Woodburn J R, Ashton S E, Curry B J, Scarlett L, Henthorn L, Richards L. Studies leading to the identification of ZD1839 (IRESSA): an orally active, selective epidermal growth factor receptor tyrosine kinase inhibitor targeted to the treatment of cancer. Bioorg Med Chem Lett. 2001 Jul. 23; 11(14):1911-4.

Blotnick, S., Peoples, G. E., Freeman, M. R., Eberlein, T. J. & Klagsbrun, M. T lymphocytes synthesize and export heparin-binding epidermal growth factor-like growth factor and basic fibroblast growth factor, mitogens for vascular cells and fibroblasts: differential production and release by CD4+ and CD8+ T cells. Proc Natl Acad Sci USA 91, 2890-94 (1994).

Boucher, A., Droz, D., Adafer, E. & Noel, L. H. Relationship between the integrity of Bowman's capsule and the composition of cellular crescents in human crescentic glomerulonephritis. Lab Invest 56, 526-33 (1987).

Bridges A J, Zhou H, Cody D R, Rewcastle G W, McMichael A, Showalter H D, Fry D W, Kraker A J, Denny W A (1996) "Tyrosine kinase inhibitors. 8. An unusually steep structure-activity relationship for analogues of 4-(3-bromoanilino)-6,7-dimethoxy-quinazoline (PD 153035), a potent inhibitor of the epidermal growth factor receptor" J. Med. Chem. 39(1):267-76

Brummelkamp T R, Bernards R, Agami R. A system for stable expression of short interfering RNAs in mammalian cells. Science. 2002 Apr. 19; 296(5567):550-3.

Chan K C, Knox W F, Gee J M, Morris J, Nicholson R I, Potten C S, Bundred N J. Effect of epidermal growth factor receptor tyrosine kinase inhibition on epithelial proliferation in normal and premalignant breast. Cancer Res. 2002 Jan. 1; 62(1):122-8.

Ciardiello F, Caputo R, Bianco R, Damiano V, Fontanini G, Cuccato S, De Placido S, Bianco A R, Tortora G. Inhibition of growth factor production and angiogenesis in human cancer cells by ZD1839 (Iressa), a selective epidermal growth factor receptor tyrosine kinase inhibitor. Clin Cancer Res. 2001 May; 7(5):1459-65.

Cote R J, Morrissey D M, Houghton A N, Beattie E J Jr, Oettgen H F, Old L J. Generation of human monoclonal antibodies reactive with cellular antigens. Proc Natl Acad Sci USA. 1983 April; 80(7):2026-30.

Couser W G, Johnson R J. Mechanisms of progressive renal disease in glomerulonephritis. Am J Kidney Dis. 1994 February; 23(2):193-8.

Couser W G. Pathogenesis of glomerular damage in glomerulonephritis. Nephrol Dial Transplant. 1998; 13 Suppl 1:10-5.

Cunnick J M, Dorsey J F, Standley T, Turkson J, Kraker A J, Fry D W, Jove R, Wu J. Role of tyrosine kinase activity of epidermal growth factor receptor in the lysophosphatidic acid-stimulated mitogen-activated protein kinase pathway. J Biol Chem. 1998 Jun. 5; 273(23):14468-75.

Das, S. K., Wang, X. N., Paria, B. C., Damm, D., Abraham, J. A., Klagsbrun, M., Andrews, G. K., and Dey, S. K. 1994. Heparin-binding EGF-like growth factor gene is induced in the mouse uterus temporally by the blastocyst solely at the site of its apposition: a possible ligand for interaction with blastocyst EGF-receptor in implantation. Development, 120: 1071-1083.

Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Elenius, K., Paul, S., Allison, G., Sun, J., and Klagsbrun, M. 1997. Activation of HER4 by heparin-binding EGF-like growth factor stimulates chemotaxis but not proliferation. EMBO J., 16: 1268-1278.

Feng L, Garcia G E, Yang Y, Xia Y, Gabbai F B, Peterson O W, Abraham J A, Blantz R C, Wilson C B. Heparin-binding EGF-like growth factor contributes to reduced glomerular filtration rate during glomerulonephritis in rats. J Clin Invest. 2000 February; 105(3):341-50

Fu, S., Bottoli, I., Goller, M., and Vogt, P. K. 1999. Heparin-binding epidermal growth factor-like growth factor, a v-Jun target gene, induces oncogenic transformation. Proc. Natl. Acad. Sci. USA, 96: 5716-5721.

Goishi, K., Higashiyama, S. Klagsbrun, M., Nakano, N., Umata, T., Ishikawa, M., Mekada, E., and Taniguchi, N. 1995. Phorbol ester induces the rapid processing of cell surface heparin-binding EGF-like growth factor: conversion from juxtacrine to paracrine growth factor activity. Mol. Biol. Cell, 6: 967-980.

Goldstein N I, Prewett M, Zuklys K, Rockwell P, Mendelsohn J. Biological efficacy of a chimeric antibody to the epidermal growth factor receptor in a human tumor xenograft model. Clin Cancer Res. 1995 November; 1(11):1311-8.

Guettier, C. et al. Immunohistochemical demonstration of parietal epithelial cells and macrophages in human proliferative extra-capillary lesions. Virchows Arch A Pathol Anat Histopathol 409, 739-48 (1986).

Hancock, W. W. & Atkins, R. C. Cellular composition of crescents in human rapidly progressive glomerulonephritis identified using monoclonal antibodies. Am J Nephrol 4, 177-81 (1984).

Hannon G J. RNA interference. Nature. 2002 Jul. 11; 418 (6894):244-51.

Higashiyama, S., Abraham, J. A., and Klagsbrun, M. 1993. Heparin-binding EGF-like growth factor stimulation of smooth muscle cell migration: dependence on interactions with cell surface heparan sulfate. J. Cell Biol., 122: 933-940.

Higashiyama, S., Abraham, J. A., Miller, J., Fiddes, J. C., and Klagsbrun, M. 1991. A heparin-binding growth factor secreted by macrophage-like cells that is related to EGF. Science, 251: 936-939.

Higashiyama, S., Iwamoto, R., Goishi, K., Raab, G., Taniguchi, N., Klagsbrun, M., and Mekada, E. 1995. The membrane protein CD9/DRAP27 potentiates the juxtacrine growth factor activity of the membrane-anchored heparin-binding EGF-like growth factor. J. Cell Biol., 128: 929-938.

Higashiyama, S., Lau, K., Besner, G. E., Abraham, J. A., and Klagsbrun, M. 1992. Structure of heparin-binding EGF-like growth factor. Multiple forms, primary structure, and glycosylation of the mature protein. J. Biol. Chem., 267: 6205-6212.

Huang S M, Bock J M, Harari P M. Epidermal growth factor receptor blockade with C225 modulates proliferation, apoptosis, and radiosensitivity in squamous cell carcinomas of the head and neck. Cancer Res. 1999 Apr. 15; 59(8):1935-40.

Huse W D, Sastry L, Iverson S A, Kang A S, Alting-Mees M, Burton D R, Benkovic S J, Lerner R A. Generation of a large combinatorial library of the immunoglobulin repertoire in phage lambda. Science. 1989 Dec. 8; 246(4935):1275-81.

Iwamoto, R. and Mekada, E. 2000. Heparin-binding EGF-like growth factor: a juxtacrine growth factor. Cytokine Growth Factor Rev., 11: 335-344.

Iwamoto, R., Handa, K., and Mekada, E. 1999. Contact-dependent growth inhibition and apoptosis of epidermal growth factor (EGF) receptor-expressing cells by the membrane-anchored form of heparin-binding EGF-like growth factor. J. Biol. Chem., 274: 25906-25912.

Iwamoto, R., Higashiyama, S., Mitamura, T., Taniguchi, N., Klagsbrun, M., and Mekada, E. 1994. Heparin-binding EGF-like growth factor, which acts as the diphtheria toxin receptor, forms a complex with membrane protein DRAP27/CD9, which up-regulates functional receptors and diphtheria toxin sensitivity. EMBO J., 13: 2322-2330.

Jackson L F, Qiu T H, Sunnarborg S W, Chang A, Zhang C, Patterson C, Lee D C. Defective valvulogenesis in HB-EGF and TACE-null mice is associated with aberrant BMP signaling. EMBO J. 2003 Jun. 2; 22(11):2704-16.

Johnson R J. The glomerular response to injury: progression or resolution? Kidney Int. 1994 June; 45(6):1769-82.

Kalluri, R., Danoff, T. M., Okada, H. & Neilson, E. G. Susceptibility to anti-glomerular basement membrane disease and Goodpasture syndrome is linked to MHC class II genes and the emergence of T cell-mediated immunity in mice. J Clin Invest 100, 2263-75 (1997).

Khong T F, Fraser S, Katerelos M, Paizis K, Hill P A, Power D A. Inhibition of heparin-binding epidermal growth factor-like growth factor increases albuminuria in puromycin aminonucleoside nephrosis. Kidney Int. 2000 September; 58(3):1098-107.

Kim T E, Murren J R. Lapatinib ditosylate GlaxoSmithKline. IDrugs. 2003 September; 6(9):886-93.

Kimura, R., Iwamoto, R., and Mekada, E. 2005. Soluble form of heparin-binding EGF-like growth factor contributes to retinoic acid-induced epidermal hyperplasia. Cell Struct. Funct., 30: 35-42.

Kirkland, G., Paizis, K., Wu, L. L., Katerelos, M. & Power, D. A. Heparin-binding EGF-like growth factor mRNA is upregulated in the peri-infarct region of the remnant kidney model: in vitro evidence suggests a regulatory role in myofibroblast transformation. J Am Soc Nephrol 9, 1464-73 (1998).

Kohler G, Milstein C. Continuous cultures of fused cells secreting antibody of predefined specificity. Nature. 1975 Aug. 7; 256(5517):495-7.

Kume, N. & Gimbrone, M. A., Jr. Lysophosphatidylcholine transcriptionally induces growth factor gene expression in cultured human endothelial cells. J Clin Invest 93, 907-11 (1994).

Lee, Y. J., Shin, S. J., Lin, S. R., Tan, M. S. & Tsai, J. H. Increased expression of heparin binding epidermal growth-factor-like growth factor mRNA in the kidney of streptozotocin-induced diabetic rats. Biochem Biophys Res Commun 207, 216-22 (1995).

Levy, J. B. & Pusey, C. D. Anti-glomerular basement membrane disease. in Oxford Textbook of Medicine, 4th Edition (eds. Warrell, D. A., Cox, T. M. & Firth, J. D.) (Oxford University Press, Oxford, 2003).

Levy, J. B., Turner, A. N., Rees, A. J. & Pusey, C. D. Long-term outcome of anti-glomerular basement membrane antibody disease treated with plasma exchange and immunosuppression. Ann Intern Med 134, 1033-42 (2001).

Lloyd C M, Minto A W, Dorf M E, Proudfoot A, Wells T N, Salant D J, Gutierrez-Ramos J C. RANTES and monocyte chemoattractant protein-1 (MCP-1) play an important role in the inflammatory phase of crescentic nephritis, but only MCP-1 is involved in crescent formation and interstitial fibrosis. J Exp Med. 1997 Apr. 7; 185(7):1371-80.

Marikovsky, M., Breuing, K., Liu, P. Y., Eriksson, E., Higashiyama, S., Farber, R, Abraham, J., and Klagsbrun, M. 1993. Appearance of heparin-binding EGF-like growth factor in wound fluid as a response to injury. Proc. Natl. Acad. Sci. USA, 90: 3889-3893.

Massague, J. and Pandiella, A. 1993. Membrane-anchored growth factors. Annu. Rev. Biochem., 62: 515-541.

McManus M T, Sharp P A. Gene silencing in mammals by small interfering RNAs. Nat Rev Genet. 2002 October; 3(10): 737-47.

Mine, N., Iwamoto, R., and Mekada, E. 2005. HB-EGF promotes epithelial cell migration in eyelid development. Development, 132: 4317-4326.

Mitamura, T., Higashiyama, S., Taniguchi, N., Klagsbrun, M. and Mekada, E. (1995) Diphtheria toxin binds to the epidermal growth factor (EGF)-like domain of human heparin-binding EGF-like growth factor/diphtheria toxin receptor and inhibits specifically its mitogenic activity. J. Biol. Chem., 270, 1015-1019.

Moasser M M, Basso A, Averbuch S D, Rosen N. The tyrosine kinase inhibitor ZD1839 ("Iressa") inhibits HER2-driven signaling and suppresses the growth of HER2-overexpressing tumor cells. Cancer Res. 2001 Oct. 1; 61(19):7184-8.

Modjtahedi H, Styles J M, Dean C J. The human EGF receptor as a target for cancer therapy: six new rat mAbs against the receptor on the breast carcinoma MDA-MB 468. Br J Cancer. 1993 February; 67(2):247-53.

Moss M L, Jin S L, Milla M E, Bickett D M, Burkhart W, Carter H L, Chen W J, Clay W C, Didsbury J R, Hassler D, Hoffman C R, Kost T A, Lambert M H, Leesnitzer M A, McCauley P, McGeehan G, Mitchell J, Moyer M, Pahel G, Rocque W, Overton L K, Schoenen F, Seaton T, Su J L, Becherer J D, Cloning of a disintegrin metalloproteinase that processes precursor tumour-necrosis factor-alpha. Nature. 1997 Feb. 20; 385(6618):733-6

Moulder S L, Yakes F M, Muthuswamy S K, Bianco R, Simpson J F, Arteaga C L. Epidermal growth factor receptor (HER1) tyrosine kinase inhibitor ZD1839 (Iressa) inhibits HER2/neu (erbB2)-overexpressing breast cancer cells in vitro and in vivo. Cancer Res. 2001 Dec. 15; 61(24):8887-95.

Moyer J D, Barbacci E G, Iwata K K, Arnold L, Boman B, Cunningham A, DiOrio C, Doty J, Morin M J, Moyer M P, Neveu M, Pollack V A, Pustilnik L R, Reynolds M M, Sloan D, Theleman A, Miller P. Induction of apoptosis and cell cycle arrest by CP-358,774, an inhibitor of epidermal growth factor receptor tyrosine kinase. Cancer Res. 1997 Nov. 1; 57(21): 4838-48.

Naglich, J. G., Metherall, J. E., Russell, D. W., and Eidels, L. 1992. Expression cloning of a diphtheria toxin receptor: identity with a heparin-binding EGF-like growth factor precursor. Cell, 69: 1051-1061.

Nakamura, K., Iwamoto, R., and Mekada, E. 1995. Membrane-anchored heparin-binding EGF-like growth factor (HB-EGF) and diphtheria toxin receptor-associated protein (DRAP27)/CD9 form a complex with integrin a3131 at cell-cell contact sites. J. Cell Biol., 129: 1691-1705.

Ng Y Y, Fan J M, Mu W, Nikolic-Paterson D J, Yang W C, Huang T P, Atkins R C, Lan H Y. Glomerular epithelial-myofibroblast transdifferentiation in the evolution of glomerular crescent formation. Nephrol Dial Transplant. 1999 December; 14(12):2860-72.

Nikolic-Paterson, D. J. & Atkins, R. C. The role of macrophages in glomerulonephritis. Nephrol Dial Transplant 16 Suppl 5, 3-7 (2001).

Osherov, N. & Levitzki, A. Epidermal-growth-factor-dependent activation of the src-family kinases. Eur J Biochem 225, 1047-53 (1994).

Paizis K, Kirkland G, Polihronis M, Katerelos M, Kanellis J, Power D A. Heparin-binding epidermal growth factor-like growth factor in experimental models of membranous and minimal change nephropathy. Kidney Int. 1998 May; 53(5): 1162-71.

Peoples G E, Blotnick S, Takahashi K, Freeman M R, Klagsbrun M, Eberlein T J. T lymphocytes that infiltrate tumors and atherosclerotic plaques produce heparin-binding epidermal growth factor-like growth factor and basic fibroblast growth factor: a potential pathologic role. Proc Natl Acad Sci USA. 1995 Jul. 3; 92(14):6547-51.

Polihronis, M., Murphy, B. F., Pearse, M. J. & Power, D. A. Heparin-binding epidermal growth factor-like growth factor, an immediate-early gene for mesangial cells, is up-regulated in the Thy-1.1 model. Exp Nephrol 4, 271-8 (1996).

Powell, P. P., Klagsbrun, M., Abraham, J. A., and Jones, R. C. 1993. Eosinophils expressing heparin-binding EGF-like growth factor mRNA localize around lung microvessels in pulmonary hypertension. Am. J. Pathol., 143: 784-793.

Prenzel N, Fischer O M, Streit S, Hart S, Ullrich A. The epidermal growth factor receptor family as a central element for cellular signal transduction and diversification. Endocr Relat Cancer. 2001 March; 8(1):11-31.

Raab, G. and Klagsbrun, M. 1997. Heparin-binding EGF-like growth factor. Biochim. Biophys. Acta, 1333: F179-F199.

Ranson M, Hammond L A, Ferry D, Kris M, Tullo A, Murray P I, Miller V, Averbuch S, Ochs J, Morris C, Feyereislova A, Swaisland H, Rowinsky E K. ZD1839, a selective oral epidermal growth factor receptor-tyrosine kinase inhibitor, is well tolerated and active in patients with solid, malignant tumors: results of a phase I trial. J Clin Oncol. 2002 May 1; 20(9):2240-50.

Rewcastle G W, Murray D K, Elliott W L, Fry D W, Howard C T, Nelson J M, Roberts B J, Vincent P W, Showalter H D, Winters R T, Denny W A. Tyrosine kinase inhibitors. 14. Structure-activity relationships for methylamino-substituted derivatives of 4-[(3-bromophenyl)amino]-6-(methylamino)-pyrido[3,4-d]pyrimidine (PD 158780), a potent and specific inhibitor of the tyrosine kinase activity of receptors for the EGF family of growth factors. J Med Chem. 1998 Feb. 26; 41(5):742-51.

Salama, A. D., Levy, J. B., Lightstone, L. & Pusey, C. D. Goodpasture's disease. Lancet 358, 917-20 (2001).

Shirakata, Y., Kimura, R., Nanba, D., Iwamoto, R., Tokumaru, S., Morimoto, C., Yokota, K., Nakamura, M., Sayama, K., Mekada, E., Higashiyama, S., and Hashimoto, K. 2005. Heparin-binding EGF-like growth factor accelerates keratinocyte migration and skin wound healing. J. Cell Sci., 118: 2363-2370.

Slichenmyer W J, Elliott W L, Fry D W. CI-1033, a pan-erbB tyrosine kinase inhibitor. Semin Oncol. 2001 October; 28(5 Suppl 16):80-5.

Smaill J. B., Palmer B. D., Rewcastle G. W., Denny W. A., McNamara D. J., Dobrusin E. M., Bridges A. J., Zhou H., Showalter H. D., Winters R. T., Leopold W. R., Fry D. W., Nelson J. M., Slintak V., Elliot W. L., Roberts B. J., Vincent P. W., Patmore S. J. Tyrosine kinase inhibitors 15.4-(phenylamino)quinazoline and 4-(phenylamino)pyrido[d]pyrimidine acrylamides as irreversible inhibitors of the ATP binding site of the epidermal growth factor receptor. J. Med. Chem., 42: 1803-1815, 1999.

Smaill J B, Rewcastle G W, Loo J A, Greis K D, Chan O H, Reyner E L, Lipka E, Showalter H D, Vincent P W, Elliott W L, Denny W A. Tyrosine kinase inhibitors. 17. Irreversible inhibitors of the epidermal growth factor receptor: 4-(phenylamino)quinazoline- and 4-(phenylamino)pyrido[3,2-d]pyrimidine-6-acrylamides bearing additional solubilizing functions. J Med Chem. 2000 Apr. 6; 43(7):1380-97.

Takemura T, Murata Y, Hino S, Okada M, Yanagida H, Ikeda M, Yoshioka K. Heparin-binding EGF-like growth factor is expressed by mesangial cells and is involved in mesangial proliferation in glomerulonephritis. J Pathol. 1999 November; 189(3):431-8.

Teramoto T, Onda M, Tokunaga A, Asano G. Inhibitory effect of anti-epidermal growth factor receptor antibody on a human gastric cancer. Cancer. 1996 Apr. 15; 77(8 Suppl): 1639-45.

Tipping, P. G. & Holdsworth, S. R. T cells in glomerulonephritis. Springer Semin Immunopathol 24, 377-93 (2003).

Tokumaru, S., Higashiyama, S., Endo, T., Nakagawa, T., Miyagawa, J. I., Yamamori, K., Hanakawa, Y., Ohmoto, H., Yoshino, K., Shirakata, Y., Matsuzawa, Y., Hashimoto, K., and Taniguchi, N. 2000. Ectodomain shedding of epidermal growth factor receptor ligands is required for keratinocyte migration in cutaneous wound healing. J. Cell Biol., 151: 209-220.

Topham P S, Csizmadia V, Soler D, Hines D, Gerard C J, Salant D J, Hancock W W. Lack of chemokine receptor CCR1 enhances Th1 responses and glomerular injury during nephrotoxic nephritis. J Clin Invest. 1999 December; 104(11): 1549-57.

Traxler P, Bold G, Buchdunger E, Caravatti G, Furet P, Manley P, O'Reilly T, Wood J, Zimmermann J. Tyrosine kinase inhibitors: from rational design to clinical trials. Med Res Rev. 2001 November; 21(6):499-512.

Traxler P., Buchdunger E., Furet P., Gschwind H—P., Ho P., Mett H., O'Reilly T., Pfaar U., Thomas H. Preclinical profile of PKI166—a novel and potent EGF-R tyrosine kinase inhibitor for clinical development (abstr.) Clin. Cancer Res., 5: 3750s 1999.

Traxler P M (1998) Tyrosine kinase inhibitors in cancer treatment (oart II). Exp Opin Ther Patents (UK) δ: 1599-1625.

Traxler P M, Furet P, Mett-H, Buchdunger E, Meyer T, Lydon N. 4-(Phenylamino)pyrrolopyrimidines: potent and selective, ATP site directed inhibitors of the EGF-receptor protein tyrosine kinase. J Med Chem. 1996 Jun. 7; 39(12): 2285-92.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Ullrich A, Coussens L, Hayflick J S, Dull T J, Gray A, Tam A W, Lee J, Yarden Y, Libermann T A, Schlessinger J, et al. Human epidermal growth factor receptor cDNA sequence and aberrant expression of the amplified gene in A431 epidermoid carcinoma cells. Nature. 1984 May 31-Jun. 6; 309 (5967):418-25.

Ward W H, Cook P N, Slater A M, Davies D H, Holdgate G A, Green L R. Epidermal growth factor receptor tyrosine kinase. Investigation of catalytic mechanism, structure-based searching and discovery of a potent inhibitor. Biochem Pharmacol. 1994 Aug. 17; 48(4):659-66.

Woodburn J. R., Barker A. J., Gibson K. H., Ashton S. E., Wakeling A. E., Curry B. J., Scarlett L., Henthorn L. R. ZD1839, an epidermal growth factor receptor tyrosine kinase inhibitor selected for clinical development. Proc. Am. Assoc. Cancer Res., 38: 4251 1997.

Yang X D, Jia X C, Corvalan J R, Wang P, Davis C G, Jakobovits A. Eradication of established tumors by a fully human monoclonal antibody to the epidermal growth factor receptor without concomitant chemotherapy. Cancer Res. 1999 Mar. 15; 59(6):1236-43.

Yoshizumi M, Kourembanas S, Temizer D H, Cambria R P, Quertermous T, Lee M E. Tumor necrosis factor increases transcription of the heparin-binding epidermal growth factor-like growth factor gene in vascular endothelial cells. J Biol Chem. 1992 May 15; 267(14):9467-9.

The invention claimed is:

1. A method for treating immune-mediated glomerulonephritis, comprising administering a subject in need thereof with a therapeutically effective amount of an EGFR antagonist wherein said immune-mediated glomerulonephritis is the crescentic glomerulonephritis.

2. The method according to claim 1, wherein said EGFR antagonist is selected in the group consisting of erlotinib, gefitinib, canertinib, PD169540, PD-158780, AG1478, PD153035, CGP59326, PKI166, EKB569, or GW572016.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer HB-EGF

<400> SEQUENCE: 1
ttcccagaca ggatctcacc                                              20

<210> SEQ ID NO 2
<211> LENGTH: 20
<212> TYPE: DNA
<213> ORGANISM: Artificial Sequence
<220> FEATURE:
<223> OTHER INFORMATION: primer HB-EGF

<400> SEQUENCE: 2
gtgggtagca gctggtttgt                                              20

<210> SEQ ID NO 3
<211> LENGTH: 20
<212> TYPE: DNA
<213> ORGANISM: Artificial Sequence
<220> FEATURE:
<223> OTHER INFORMATION: primer 18S

<400> SEQUENCE: 3
gagcgaaagc atttgccaag                                              20

<210> SEQ ID NO 4
<211> LENGTH: 20
<212> TYPE: DNA
<213> ORGANISM: Artificial Sequence
```

```
<220> FEATURE:
<223> OTHER INFORMATION: primer 18S

<400> SEQUENCE: 4
ggcatcgttt atggtcggaa                                              20
```